(12) United States Patent
Sathe et al.

(10) Patent No.: US 8,741,962 B2
(45) Date of Patent: Jun. 3, 2014

(54) PROCESS FOR PREPARATION OF RASAGILINE AND SALTS THEREOF

(75) Inventors: Dhananjay Govind Sathe, Maharashtra (IN); Subhash Vishwanath Damle, Maharashtra (IN); Kamlesh Digambar Sawant, Maharashtra (IN); Parag Sukumar Gatne, Maharashtra (IN); Tushar Anil Naik, Maharashtra (IN)

(73) Assignee: USV Limited (IN)

( * ) Notice: Subject to any disclaimer, the term of this patent is extended or adjusted under 35 U.S.C. 154(b) by 524 days.

(21) Appl. No.: 12/954,497

(22) Filed: Nov. 24, 2010

(65) Prior Publication Data
US 2011/0155626 A1 Jun. 30, 2011

(30) Foreign Application Priority Data

Nov. 26, 2009 (IN) .......................... 2733/MUM/2009
Aug. 10, 2010 (IN) .......................... 2250/MUM/2010

(51) Int. Cl.
*A01N 33/02* (2006.01)
*A61K 31/135* (2006.01)

(52) U.S. Cl.
USPC .......................................... 514/647; 514/657

(58) Field of Classification Search
USPC .......................................................... 514/647
See application file for complete search history.

(56) References Cited

U.S. PATENT DOCUMENTS

2006/0094783 A1* 5/2006 Youdim et al. ................. 514/554
2007/0272894 A1* 11/2007 Ma ........................... 252/182.12

FOREIGN PATENT DOCUMENTS

WO  WO 2006091657 A1 *  8/2006
WO  WO 2009147432 A1 * 12/2009
WO  WO 2011121607 A2 * 10/2011

* cited by examiner

*Primary Examiner* — Layla Soroush
(74) *Attorney, Agent, or Firm* — Schwegman, Lundberg & Woessner, P.A.

(57) ABSTRACT

The present invention relates to an improved process for the preparation of Rasagiline or pharmaceutically acceptable salts thereof. The present invention also relates to Rasagiline salts, polymorphs thereof and process for preparation thereof.

15 Claims, 11 Drawing Sheets

PROCESS FOR PREPARATION OF RASAGILINE AND SALTS THEREOF

RELATED APPLICATION

This application claims the benefit of Indian Provisional Application No. 2733/MUM/2009, filed on Nov. 26, 2009, Entitled: Crystalline form of Rasagiline and Process for Preparation thereof and also claims the benefit of Indian Provisional Application No. 2250/MUM/2010, filed on Aug. 10, 2010, Entitled: Process for Preparation of Rasagiline and salts thereof, which applications are incorporated in their entirety.

FIELD OF THE INVENTION

The present invention relates to an improved process for the preparation of Rasagiline or pharmaceutically acceptable salts thereof. The present invention also relates to Rasagiline salts of formula (I), polymorphs thereof and process for preparation thereof.

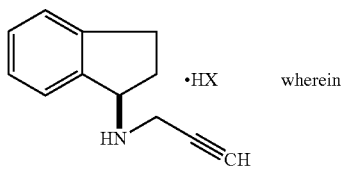

(I)

X is a suitable anion such as mesylate, chloride, bromide, palmitate and the like

BACKGROUND AND PRIOR ART

Rasagiline is a chemical inhibitor of enzyme monoamine oxidase (MAO) type B which has a major role in the inactivation of biogenic and diet derived amines in the central nervous system. MAO has two isozymes (types A and B) and type B is responsible for metabolising dopamine in the central nervous system; as dopamine deficiency is the main contributing factor to the clinical manifestations of Parkinson's disease, inhibition of MAO-B should tend to restore dopamine levels towards normal values and this improves the condition. Rasagiline was developed for the symptomatic treatment of Parkinson's disease both as monotherapy in early disease and as adjunct therapy to levodopa+aminoacids decarboxylase inhibitor (LD+ADI) in patients with motor fluctuations. Parkinson's disease is a common neurodegenerative disorder typified by loss of dopaminergic neurones from the basal ganglia and by a characteristic clinical syndrome with cardinal physical signs of resting tremor, bradikinesia and rigidity. The main treatment aims at alleviating symptoms through a balance of anti-cholinergic and dopaminergic drugs.

Rasagiline mesylate, chemically known as 1H-Inden-1-amine, 2,3-dihydro-N-2-propynyl-, (1R)-, methanesulfonate or N-propargyl-1(R)-aminoindan mesylate, is approved for the treatment of Parkinson's disease and marketed under the name AZILECT® by Teva. Scientific discussion for Azilect states that two salts were used during the non-clinical programme. Initially the hydrochloride salt was used but this was changed to the mesylate salt to overcome stability issues. Inhibition of MAO activity by rasagiline mesylate, rasagiline hydrochloride, their (S)-isomers and by the metabolite, 1-(R)-aminoindan hydrochloride was studied in vitro and ex vivo. Both Rasagiline mesylate and Rasagiline hydrochloride exhibit a similar, highly potent and MAO-B-selective inhibition activity in vitro.

EP436492 discloses process for preparation of R-(+)-Rasagiline hydrochloride which involves reaction of racemic 1-aminoindan (2) with propargyl chloride (6) in presence of potassium carbonate in acetonitrile (ACN) at 60° C. for 16 hours to obtain racemic Rasagiline base (4) which is purified using column chromatography. The ethereal solution of purified racemic base is then treated with HCl gas followed by recrystallization using isopropanol (IPA) to obtain racemic Rasagiline hydrochloride (7). R-(+)-Rasagiline is separated from the obtained racemic Rasagiline base (4) by preparative HPLC chromatography and further converted to its hydrochloride salt.

Scheme I

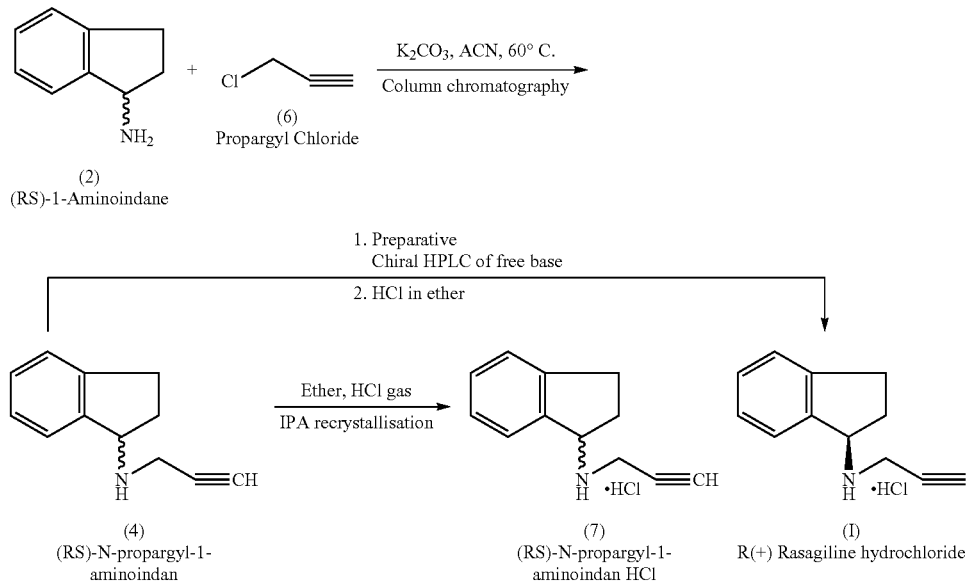

Another process for preparation of Rasagiline hydrochloride as disclosed in EP '492 comprises reaction of R(−)-1-aminoindan (8) with propargyl chloride (6) in presence of potassium carbonate in acetonitrile (ACN) at 60° C. for 16 hours to obtain R(+) Rasagiline base (9) which is then purified by column chromatography. The purified base is then converted to R(+)-Rasagiline hydrochloride followed by recrystallization with isopropanol. The main disadvantage of this process is longer reaction time (16 hours) and low overall yield of about 56%.

Scheme II

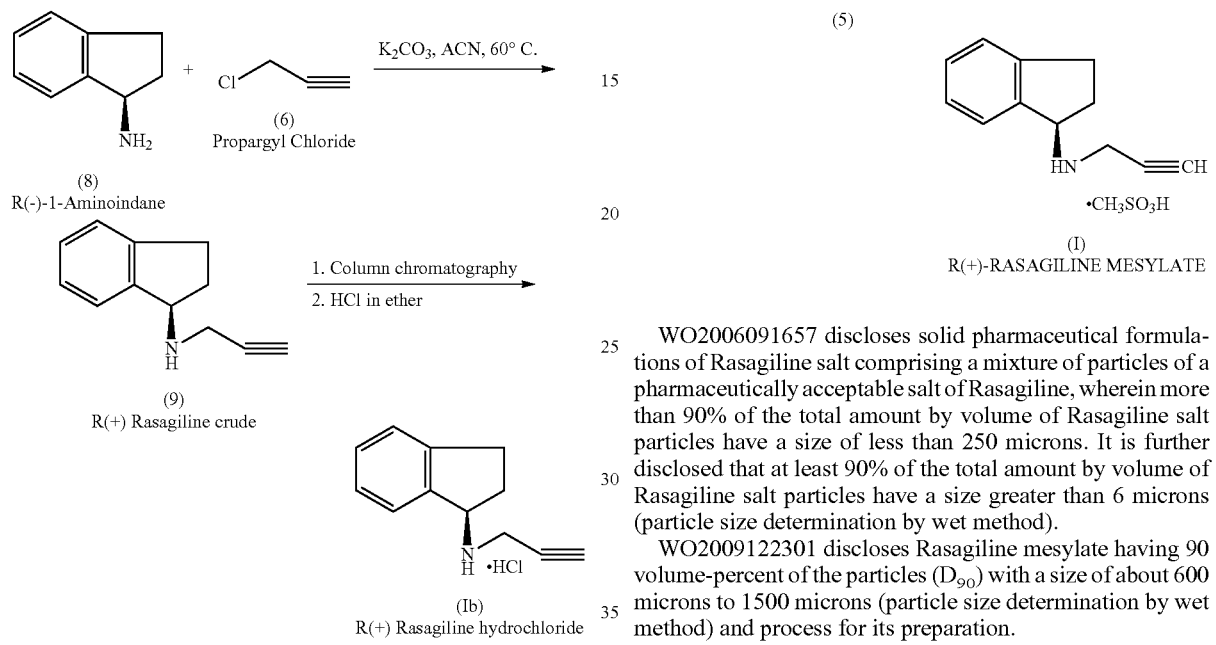

Scheme III

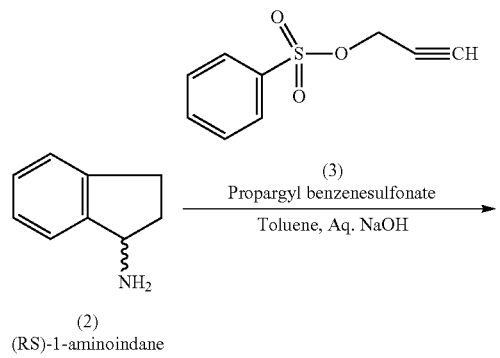

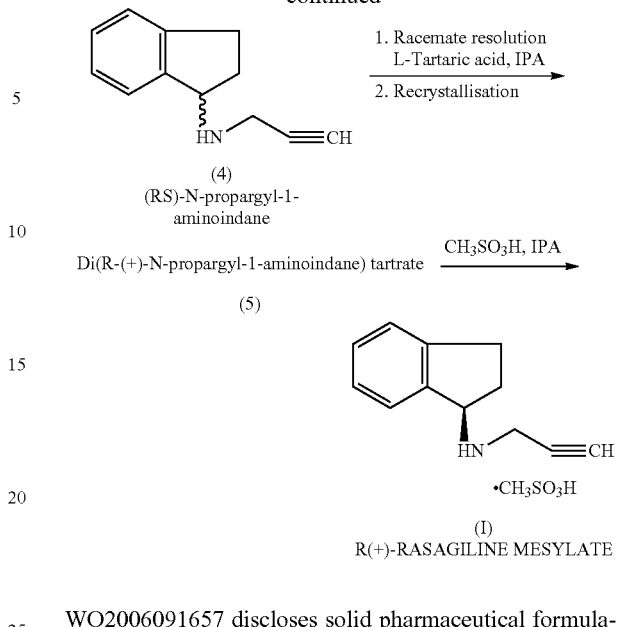

WO2006091657 discloses solid pharmaceutical formulations of Rasagiline salt comprising a mixture of particles of a pharmaceutically acceptable salt of Rasagiline, wherein more than 90% of the total amount by volume of Rasagiline salt particles have a size of less than 250 microns. It is further disclosed that at least 90% of the total amount by volume of Rasagiline salt particles have a size greater than 6 microns (particle size determination by wet method).

WO2009122301 discloses Rasagiline mesylate having 90 volume-percent of the particles ($D_{90}$) with a size of about 600 microns to 1500 microns (particle size determination by wet method) and process for its preparation.

WO2010059913 describes processes for the preparation of Rasagiline mesylate comprising reacting 1-indanone with propargylamine or a salt thereof in the presence of a solvent to afford N-(2-propynyl)-indanylimine or a salt thereof which is optionally isolated. The obtained N-(2-propynyl)-indanylimine or a salt thereof is reduced with a reducing agent to afford racemic Rasagiline. The obtained racemic Rasagiline is treated with chiral resolving agent to get diastereomeric salt; optionally isolating the free base of diastereomeric salt. The obtained free base or diastereomeric salt is reacted with acid in solvent to get acid addition salt of R(+)-Rasagiline. WO '913 also discloses Rasagiline mesylate having 90 volume percent of the particles ($D_{90}$) with sizes less than about 6 μm and processes for the preparation thereof.

U.S. Pat. No. 7,491,847 discloses methods of isolation of secondary propargylated aminoindan derivatives from a reaction mixture.

There exists a need to develop a simple and commercially viable process for the preparation of R(+)-Rasagiline and its salts. The present invention provides industrially viable process for preparation of R(+)-Rasagiline or pharmaceutically acceptable salt thereof, such as mesylate, hydrobromide and hydrochloride salt of Rasagiline in high yield and purity. The inventors of the present invention have studied the various salts of Rasagiline. It is known that salts of active pharmaceutical ingredients (APIs) are used in drug formulations because of improved properties with respect to solubility, stability or bioavailability. The present invention deals with a novel salt of R(+)-Rasagiline, R(+)-Rasagiline palmitate and process for preparation thereof.

The inventors of the present invention have also studied polymorphism in Rasagiline and its salts. Polymorphism is the ability of a compound to exhibit more than one orientation or conformation of molecules within the crystal lattice. Many organic compounds, including active pharmaceutical ingredient (API), exhibit polymorphism. Drug substances may exist in various polymorphic forms, which may differ from each other in terms of stability, solubility, compressibility, flowability and spectroscopic properties, thus affecting dissolution, bioavailability and handling characteristics of the substance. Rate of dissolution of an API in a patient's stomach fluid can have therapeutic consequences since it imposes an upper limit on the rate at which an orally administrated API can reach the patient's bloodstream. Flowability affects the ease with which the material is handled while processing a pharmaceutical product. Knowledge of the existence of different crystal phases and their overall physical and chemical behavior is required for selection of a polymorphic form for use in the preparation of a final dosage form. It is preferred to have a single, pure and stable polymorphic form in the final drug product. To this end, investigation of crystal polymorphism is an essential step in pharmaceutical research due to the influence of solid-state properties on dosage form. The present invention provides polymorphs of R-(+)-Rasagiline hydrochloride and process for preparation thereof. Polymorphic forms of R-(+)-Rasagiline hydrochloride of the present invention have good flow properties, especially good bulk flow properties suitable for pharmaceutical formulation.

OBJECT OF THE PRESENT INVENTION

An object of the present invention is to provide simple and industrially feasible process for the preparation of R(+)-Rasagiline or pharmaceutically acceptable salt thereof in high yield and high purity.

Another object of the present invention is to provide a process for recovery of R(−)-1-aminoindan and converting it to R(+)-Rasagiline or pharmaceutically acceptable salt thereof.

Another object of the present invention provides R(+)-Rasagiline or salt thereof substantially free from impurity, (1S)-2,3-dihydro-N-2-propynyl-1H-indane-1-amine and genotoxic impurities viz., propargyl benzenesulfonate and isopropyl mesylate.

Yet another object of the present invention is to provide impurity A, namely N-2-Propene-1-yl-2-bromo-(R)-aminoindan hydrobromide and impurity B, namely N-2-Propene-1-yl-3-bromo-(R)-aminoindan hydrobromide and use thereof as reference marker/reference standard for determining purity of R(+)-Rasagiline or pharmaceutically acceptable salt thereof, in particular R(+)-Rasagiline hydrobromide.

Another object of the present invention is to provide substantially pure R(+)-Rasagiline salts having particles such that $d_{90}$ is about 4-9µ, $d_{50}$ is about 2-4µ and $d_{10}$ is about 1-2µ.

Another object of the present invention provides a dry method for particle size determination of Rasagiline and salts thereof.

Another object of the present invention is to provide a novel salt of R(+)-Rasagiline, R(+)-Rasagiline palmitate and process for preparation thereof.

Yet another object of the present invention is to provide a pack profile for packing micronized Rasagiline or its salts in order to prevent agglomeration.

Another object of the present invention is to provide polymorphic forms of R-(+)-Rasagiline hydrochloride and process for preparation thereof. Another object of the present invention is to provide a pharmaceutical composition comprising R(+)-Rasagiline and salts thereof, in particular R(+)-Rasagiline hydrobromide or R(+)-Rasagiline mesylate along with atleast one pharmaceutically acceptable excipient.

SUMMARY OF THE INVENTION

According to the present invention, there is provided a process for preparation of R(+)-Rasagiline or pharmaceutically acceptable salt thereof comprising,
    a) reacting R(−)-1-aminoindan or salt thereof with propargyl benzenesulfonate in aqueous medium to get R(+)-Rasagiline;
    b) optionally isolating R(+)-Rasagiline and/or unreacted R(−)-1-aminoindan;
    c) optionally converting R(+)-Rasagiline to pharmaceutically acceptable salt thereof.

Preferably the reaction in step a) is carried out at a temperature of 15-20° C. for about 2 to 4 hours, optionally in the presence of a phase transfer catalyst. Preferably the reaction in step a) is carried out in presence of a phase transfer catalyst selected from tetrabutyl ammonium bromide, tetrabutyl ammonium chloride, tetrabutyl ammonium hydrogen sulphate, Aliquat 336, PEG-400 or PEG-600. Preferably the pharmaceutically acceptable salt of Rasagiline is selected from the group consisting of mesylate, hydrobromide, hydrochloride and palmitate. Preferably, R(+)-Rasagiline is purified by column chromatography, prior to conversion to its pharmaceutically acceptable salt.

According to one aspect of the present invention, there is provided a process for isolation/recovery of unreacted R-(−)-1-aminoindan from the mother liquor obtained after isolation of the R(+)-Rasagiline.

According to another aspect of the present invention, there is provided R(+)-Rasagiline or pharmaceutically acceptable salt thereof substantially free of one or more of the impurities selected from the group consisting of (1S)-2,3-dihydro-N-2-propynyl-1H-indane-1-amine, propargyl benzenesulfonate and isopropyl mesylate.

Yet another aspect of the present invention provides a packaging material for Rasagiline or pharmaceutically salt thereof wherein the packaging material comprises glass bottle or polyethylene terephthalate (PET).

According to another aspect of the present invention, there is provided a novel salt of R(+)-Rasagiline, R(+)-Rasagiline palmitate.

According to another aspect of the present invention, there is provided a compound selected from Impurity A. i.e., N-2-Propene-1-yl-2-bromo-(R)-aminoindan hydrobromide and/or Impurity B. i.e., N-2-Propene-1-yl-3-bromo-(R)-aminoindan hydrobromide and use thereof as a reference marker/reference standard for determining purity of R(+)-Rasagiline or pharmaceutically acceptable salt thereof, in particular R(+)-Rasagiline hydrobromide.

Yet another aspect of the present invention provides R(+)-Rasagiline or pharmaceutically acceptable salt thereof having particle size distribution such that 90% of particles have particle size less than or equal to 9µ, and/or 50% of particles having particle size less than or equal to 4µ. Preferably, the particle size distribution is determined by dry method.

DETAILED DESCRIPTION OF THE INVENTION

Figure 1:
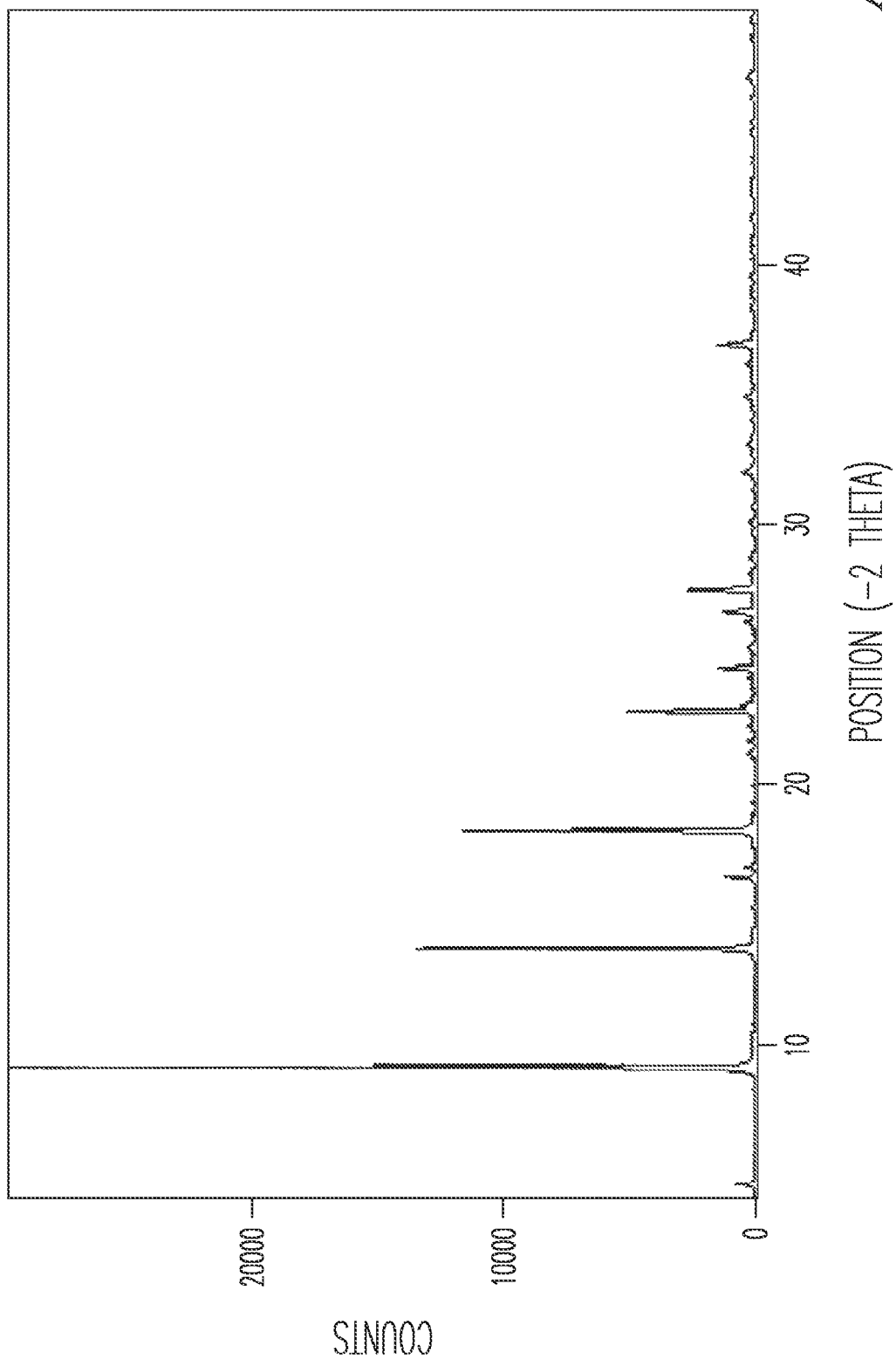
FIG. 1: X-ray powder diffraction pattern of R(+)-Rasagiline mesylate obtained according to the present invention.

The present invention provides substantially pure R(+)-Rasagiline or its pharmaceutically acceptable salts such as mesylate, hydrobromide and hydrochloride and process for preparation thereof. The present invention also provides novel salt of R(+)-Rasagiline, R(+)-Rasagiline palmitate and process for preparation thereof.

According to one embodiment of the present invention, there is provided a process for preparation of R(+)-Rasagiline or pharmaceutically acceptable salt thereof comprising,
  a) reacting R(−)-1-aminoindan or salt thereof with propargyl benzenesulfonate in aqueous medium to get R(+)-Rasagiline;
  b) optionally isolating R(+)-Rasagiline and/or unreacted R(−)-1-aminoindan;
  c) optionally converting R(+)-Rasagiline to pharmaceutically acceptable salt thereof.

In a preferred embodiment of the present invention, process for preparation of R(+)-Rasagiline comprises, reacting R-(−)-1-aminoindan hydrochloride with propargyl benzenesulfonate in an aqueous medium, preferably in presence of suitable base and phase transfer catalyst at temperature of 10-30° C. preferably at 15-20° C. for 2-4 hours, preferably 2-3 hours. After the completion of reaction, the reaction mixture is extracted with suitable solvent, preferably toluene. The combined solvent layer is washed with water. The mixture is cooled to 15-20° C. and water is added to solvent layer followed by adjusting the pH of the mixture to 3 using an acid, preferably 10% aqueous sulfuric acid solution. The separated solvent layer is washed with water. The combined aqueous layer is cooled to 15-20° C. and treated with base, preferably 10% aqueous NaOH solution to attain pH 8. The aqueous layer is extracted with suitable solvent, preferably toluene and the combined solvent layer is washed with water for isolating R(+)-Rasagiline base. The separated solvent layer is distilled under vacuum at 65° C. to get R(+)-Rasagiline as an oil.

The base used is selected from sodium carbonate, potassium carbonate, sodium bicarbonate, potassium bicarbonate, sodium hydroxide, potassium hydroxide, lithium hydroxide or mixture thereof. The phase transfer catalyst used may be selected from tetrabutyl ammonium bromide, tetrabutyl ammonium chloride, tetrabutyl ammonium hydrogen sulphate, Aliquat 336, PEG-400 or PEG-600. Solvent for extraction is selected from toluene, hexane, heptane, ethyl acetate, methyl acetate, isopropyl acetate, diisopropyl ether, methyl tertiary butyl ether or mixture thereof, preferably toluene.

Another embodiment of the present invention provides process for recovery of R(−)-1-aminoindan which comprises basification of the aqueous mother liquor obtained after separation of the solvent layer containing R(+)-Rasagiline base to get R(−)-1-aminoindan. In a preferred embodiment, the aqueous mother liquor obtained after separation of toluene layer containing R(+)-Rasagiline base is basified to pH 12-13 using a suitable base to get the starting material, R(−)-1-aminoindan.

The starting material R(−)-1-aminoindan recovered according to the present invention is further converted to Rasagiline or its pharmaceutically acceptable salt as represented in Scheme IV. The overall yield according to the present invention is about 62%.

R(+)-Rasagiline base may be purified prior to conversion to its pharmaceutically acceptable salt. Preferably, the obtained R(+)-Rasagiline base is purified by column chromatography using a suitable stationary phase and suitable solvent as mobile phase to get pure R(+)-Rasagiline substantially free from unwanted impurities. The stationary phase used for column chromatography is neutral alumina. The solvent used as mobile phase is selected from hydrocarbon, ester or mixture thereof. Hydrocarbon is selected from hexane, n-heptane, toluene or mixture thereof; Ester is selected from ethyl acetate, methyl acetate, isopropyl acetate or mixture thereof.

The starting materials used for the synthesis of Rasagiline R(−)-1-aminoindan and propargyl benzenesulfonate may be prepared by the processes known in the art. In a preferred embodiment, Propargyl benzenesulfonate is prepared by a process comprising the steps of reacting propargyl alcohol with benzene sulfonyl chloride in presence of a suitable base and a suitable solvent at a temperature of about 0-20° C., preferably 0-5° C. The base used is selected from sodium carbonate, potassium carbonate, sodium bicarbonate, potassium bicarbonate, sodium hydroxide, potassium hydroxide, lithium hydroxide or mixture thereof, preferably potassium hydroxide. Suitable solvent is selected from diethyl ether or methyl tert butyl ether. R(−)-1-aminoindan may be prepared by the process disclosed in Zhongguo Xinyao Zazhi (2009), 18(14), 1352-1353, 1371; J. Org Chem, 2006, 71, 6859-6862 or J. Org. Chem. 2007, 72, 626-629.

R(+)-Rasagiline or pharmaceutically acceptable salt thereof obtained according to the present invention is substantially free of (1S)-2,3-dihydro-N-2-propynyl-1H-indane-1-amine and genotoxic impurities.

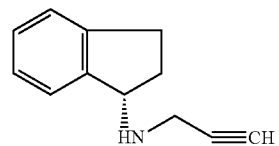

(1S)-2,3-dihydro-N-2-propynyl-1H-indane-1-amine

R(+)-Rasagiline base can be converted into pharmaceutically acceptable salt thereof by treatment with a suitable pharmaceutically acceptable acid with/without isolation of R(+)-Rasagiline base. Suitable pharmaceutically acceptable acid used for converting R(+)-Rasagiline to its pharmaceutically acceptable salt may be selected from HCl, HBr, methanesulfonic acid, palmitic acid and the like.

According to a preferred embodiment, R(+)-Rasagiline base is converted to R(+)-Rasagiline mesylate by treating the R(+)-Rasagiline base with methanesulfonic acid in suitable solvent. The reaction between Rasagiline base and methanesulfonic acid is carried out at temperature in the range of 5-25° C. The suitable solvent is $C_1$-$C_4$ straight chain or branched chain alcohols selected from methanol, ethanol, n-propanol, isopropyl alcohol, t-butanol, n-butanol, 2-ethoxyethanol, ethylene glycol or mixture thereof, preferably isopropyl alcohol. R(+)-Rasagiline mesylate obtained according to the present invention is characterized by X-ray diffraction peaks at 2θ values of about 9.07, 13.62, 16.44, 18.21, 21.17, 21.61, 22.80, 27.39 and 27.47.

The process for preparation of R(+)-Rasagiline or salt thereof according to the present invention is illustrated by the following reaction scheme:

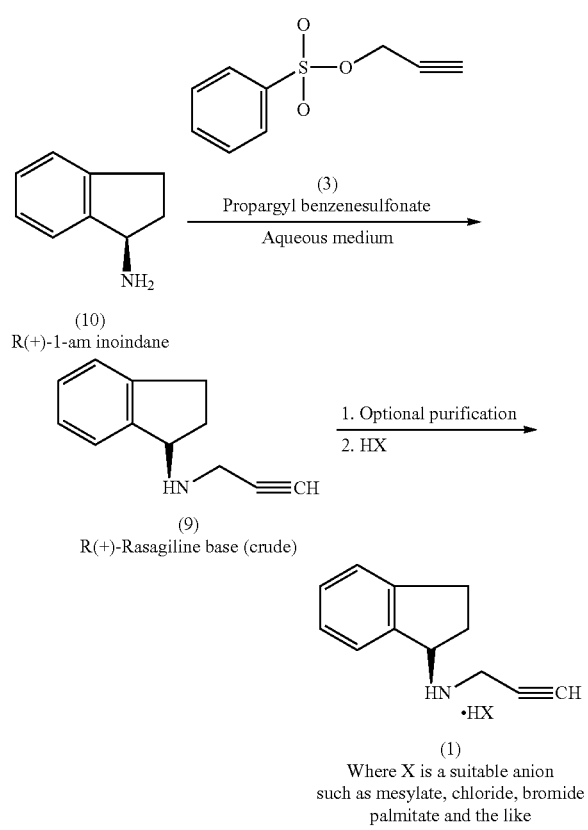

Two genotoxic impurities are reported in prior art for Rasagiline or salt thereof viz., propargyl benzenesulfonate and isopropyl mesylate. R(+)-Rasagiline or salt thereof obtained by the process of the present invention is substantially free of these genotoxic impurities, preferably not more than (NMT) about 750 ppm. In the process of the present invention, propargyl benzenesulfonate gets removed during the work up and subsequent purification by column chromatography. Isopropyl mesylate is formed by the reaction of isopropanol and methanesulfonic acid during the synthesis of Rasagiline mesylate. In the process of the present invention, the reaction is carried out at lower temperature i.e., 5-10° C. thereby avoiding the formation of isopropyl mesylate. Thus Rasagiline and pharmaceutically acceptable salts thereof prepared according to the present invention is substantially free from the above possible two genotoxic impurities.

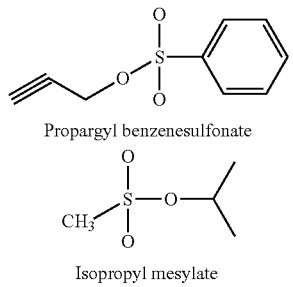

The process of the present invention provides Rasagiline mesylate in high chiral purity, ee >99.9%; chemical purity greater than 99.5% and polymorphic purity greater than 99%. The highly crystalline R(+)-Rasagiline mesylate thus obtained is passed through 25 or 30 mesh sieve to get uniform particles and the particle size is determined using Malvern Mastersizer 2000, preferably by dry method. Rasagiline mesylate obtained by the process of the present invention has particle size distribution such that $d_{90}$ is about 40-80μ, $d_{50}$ is about 10-20μ and $d_{10}$ is about 2-9μ. Rasagiline mesylate is further micronized using conventional micronization techniques. After micronization, the sample is preferably passed through 100 mesh sieve and the particle size is measured using a Malvern Mastersizer 2000 dry unit, Scirocco 2000 which is commercially available from Malvern Instruments Ltd., United Kingdom. Micronized Rasagiline mesylate has particle size distribution such that 90% of particles have particle size less than or equal to about 9μ and/or 50% of particles have particle size less than or equal to about 4μ. Preferably, $d_{90}$ is about 4-9μ, $d_{50}$ is about 2-4μ and $d_{10}$ is about 1-2μ. The specific surface area of Rasagiline mesylate is at least about 1 $m^2$/g or more.

WO2006091657 describes particle size determination of Rasagiline mesylate by wet method. The inventors of the present invention have determined the particle size distribution of Rasagiline or salts thereof by dry method.

According to another embodiment of the present invention, there is provided a method for determining the particle size of Rasagiline or salts thereof. Preferred parameters for particle size determination using dry method are provided in table below:

| Instrument | Malvern Mastersizer 2000 |
|---|---|
| Technique used | Dry mode (Sirocco 2000) |
| Sensitivity | Enhanced |
| Analysis model | General purpose |
| Vibration | 70% |
| Dispersive air pressure | 3.5 bar |
| Particle refractive index | 1.52 |
| Absorption | 0 |
| Background | 10 seconds |
| Sample measurement time | 10 seconds |
| Measurement cycle | 3 measurement per aliquot |
| Delay | 10 seconds |
| Slit width | 3 mm |
| Obscuration | 1 to 5% |

The dry method for analyzing the particle size distribution of non-micronized and micronized samples of R(+)-Rasagiline mesylate is compared with the wet method. It was found that consistent results are obtained using the dry method. Comparative results of particle size determination obtained using dry method and wet method are shown below.

|  | Particle Size Distribution (micron) of R(+)-Rasagiline mesylate before micronization | | Particle Size Distribution (micron) of R(+)-Rasagiline mesylate after micronization | |
| --- | --- | --- | --- | --- |
|  | Dry method | Wet method | Dry method | Wet method |
| Experiment 1 | | | | |
| $D_{10}$ | 3.18 | 49.24 | 1.43 | 54.52 |
| $D_{50}$ | 13.33 | 174.70 | 2.90 | 290.63 |
| $D_{90}$ | 47.11 | 832.14 | 5.74 | 1007.18 |
| Experiment 2 | | | | |
| $D_{10}$ | 3.65 | 19.81 | 1.44 | 12.91 |
| $D_{50}$ | 15.27 | 141.23 | 3.00 | 95.19 |
| $D_{90}$ | 57.38 | 590.45 | 5.94 | 796.35 |

WO2010059913 discloses that small particle size of Rasagiline mesylate is susceptible to agglomerate formation when exposed to atmosphere. Thus, the exposure of Rasagiline mesylate to the atmosphere may lead to deviation of the drug product from content uniformity requirements as a result of agglomeration. It further discloses that in order to enhance the uniformity in particle size, Rasagiline mesylate obtained after micronization is packaged under an inert atmosphere, such that the agglomerate formation is reduced. The present inventors have conducted extensive research work for solving the problem of agglomerization of micronized Rasagiline or salt thereof. The present invention thus provides specific pack profile (SPP) for packing micronized Rasagiline or salts thereof in order to prevent agglomeration.

When samples of micronized Rasagiline mesylate obtained according to the present invention are stored at room temperature in packing materials such as glass bottle or polyethylene terephthalate (PET) bottle for about one month, no agglomeration of the particles was observed. It is also observed that there is no change in XRPD pattern and particle size of the product (Table 3). However micronized Rasagiline or its salt when stored in conventional packing materials such as polythene bags or aluminum bags with inner lining of polythene resulted in agglomeration of the particles thereby resulting in loss in evenness of the particle size distribution.

TABLE 3

Specific pack profile (SPP) of Micronized Rasagiline mesylate:

|  | Micronized sample | | | After one month | | |
| --- | --- | --- | --- | --- | --- | --- |
| Package | $D_{10}$ | $D_{50}$ | $D_{90}$ | $D_{10}$ | $D_{50}$ | $D_{90}$ |
| Pack-1 (Glass bottle) | 1.40 | 3.33 | 7.88 | 1.70 | 3.66 | 7.55 |
| Pack-2 (PET bottle) | 1.43 | 2.90 | 5.74 | 1.41 | 2.97 | 5.64 |

Another embodiment of the present invention provides process for preparation of R(+)-Rasagiline hydrochloride comprising the steps of,
 a) reacting R(−)-1-aminoindan or salt thereof with propargyl benzenesulfonate in aqueous medium in presence of base and optionally in presence of phase transfer catalyst to get R(+)-Rasagiline; and
 b) converting the obtained R(+)-Rasagiline to R(+)-Rasagiline hydrochloride.

Preferably, the conversion of R(+)-Rasagiline base to R(+)-Rasagiline hydrochloride is carried out by reacting R(+)-Rasagiline base with hydrochloric acid at temperature between 5-25° C.

Yet another embodiment of the present invention provides polymorphic forms of R-(+)-Rasagiline hydrochloride and process for preparation thereof.

Figure 2:
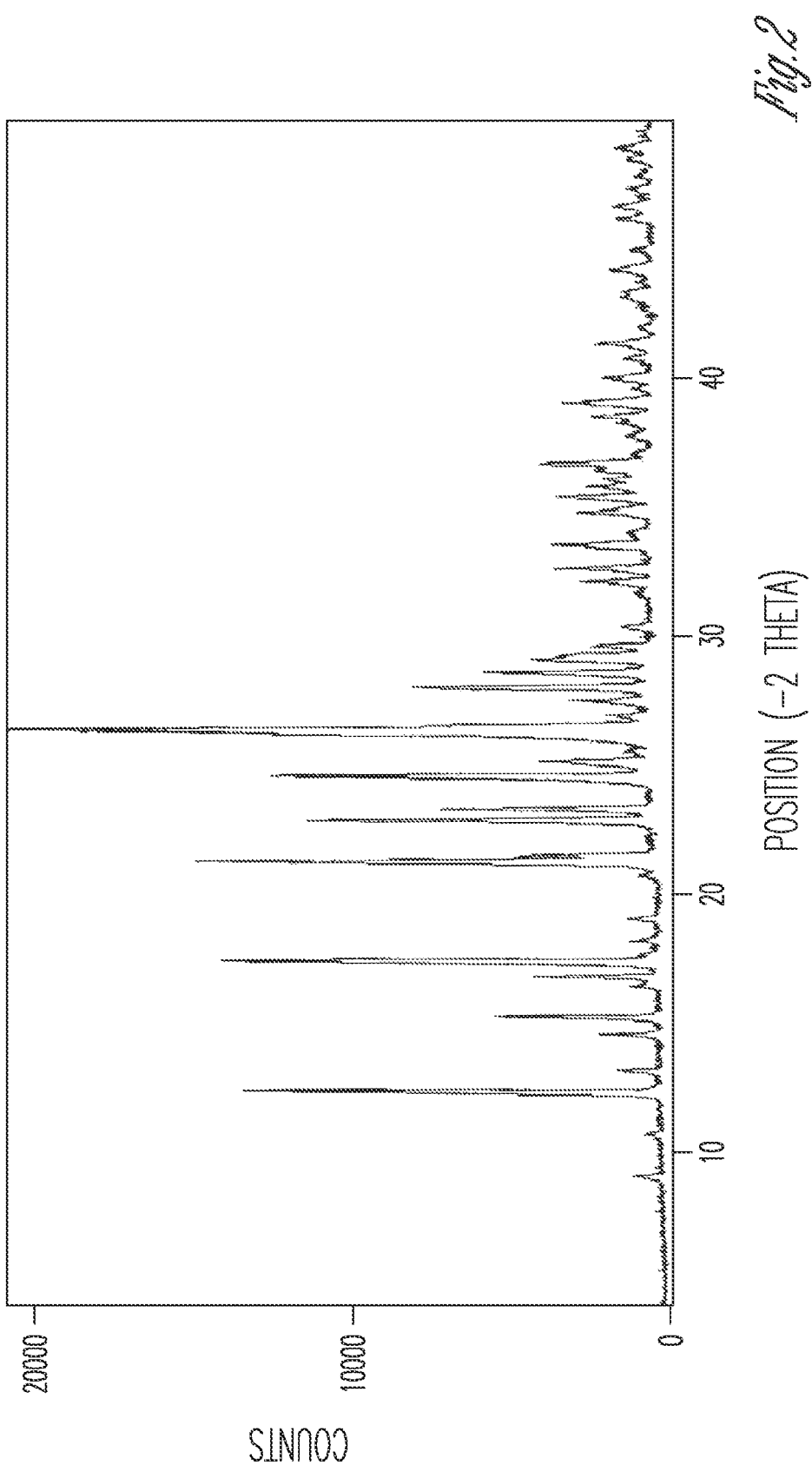
FIG. 2: X-ray powder diffraction pattern of R-(+)-Rasagiline hydrochloride obtained according to U.S. Pat. No. 5,532,415.

R-(+)-Rasagiline hydrochloride exist in polymorphic forms which are characterized and described herein. The crystalline form of R-(+)-Rasagiline hydrochloride obtained by following Example 4 of U.S. Pat. No. 5,532,415 has been designated herein as 'Form I' and characterized by X-ray Powder Diffraction pattern as shown in FIG. 2.

The present invention provides process for preparation of R-(+)-Rasagiline hydrochloride Form I comprising the steps of:
 a) dissolving Rasagiline hydrochloride in suitable solvent to get first solution;
 b) optionally adding a second solvent to the solution of step a);
 c) isolating R-(+)-Rasagiline hydrochloride Form I.

The dissolution is carried out at temperature of 25-100° C. or at reflux temperature of the solvent selected for dissolution. The solution is optionally filtered to remove insoluble/suspended impurities. In the process involving solvent-antisolvent method, the first solution is optionally cooled to a temperature of 25-30° C. before or after adding second solvent. R-(+)-Rasagiline hydrochloride Form I obtained according to present invention is substantially free of other forms and has chemical purity of more than 99% with all known impurities below 0.15% and unknown impurities below 0.1%.

Figure 3:
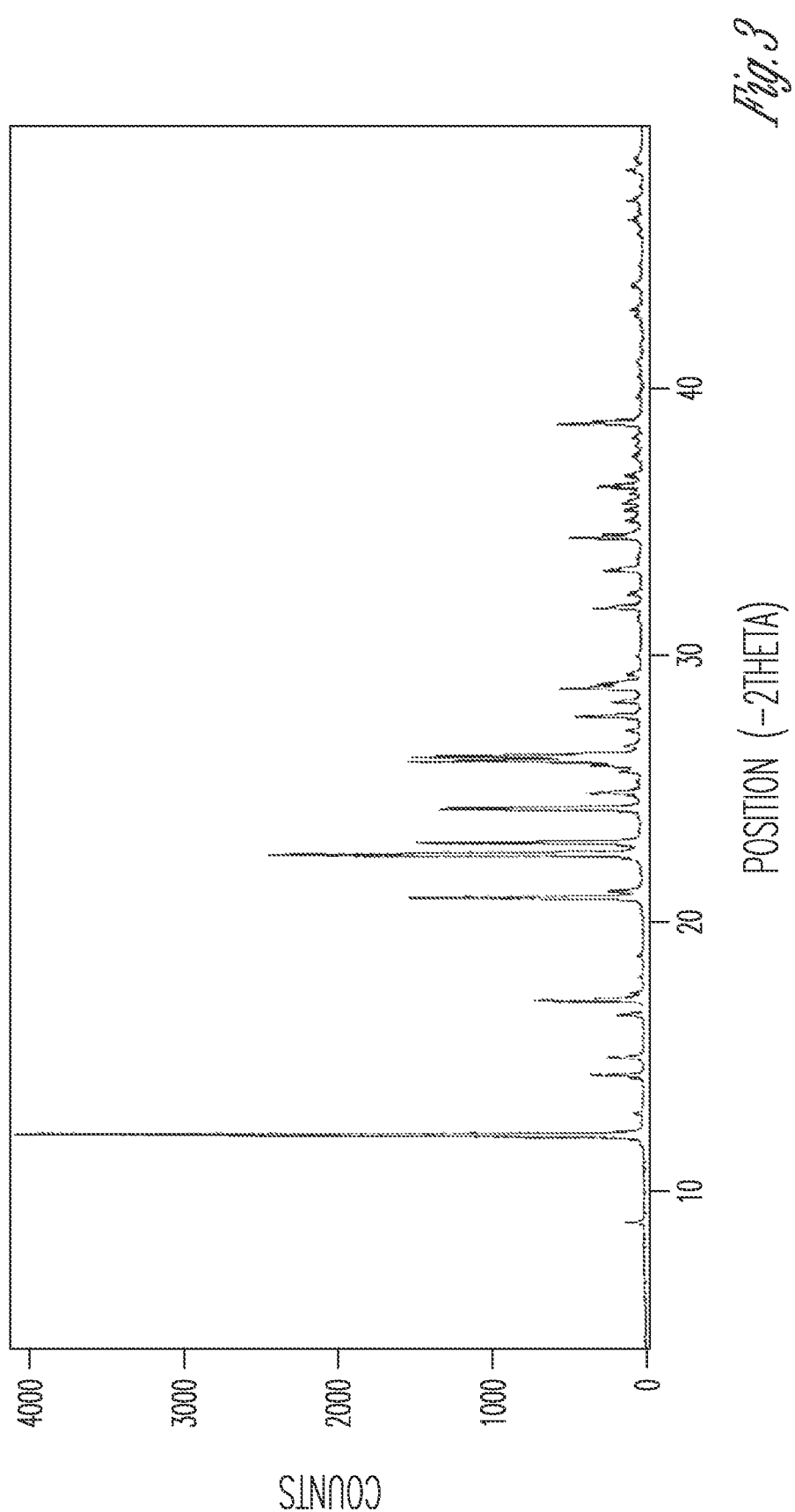
FIG. 3: X-ray powder diffraction pattern of R-(+)-Rasagiline hydrochloride Form I obtained according to present invention.
Figure 4:
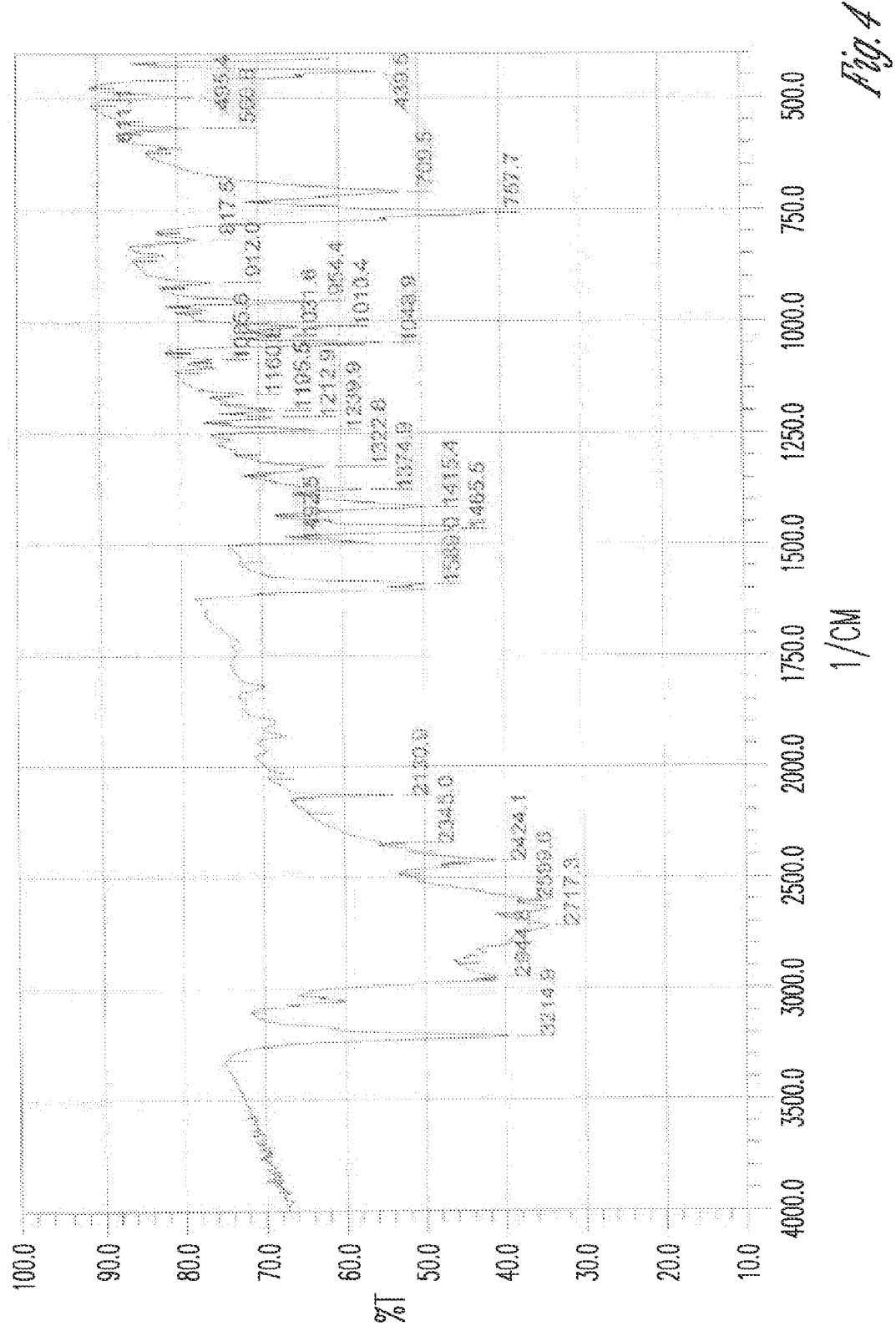
FIG. 4: FT-IR of R-(+)-Rasagiline hydrochloride Form I obtained according to present invention.
Figure 5:
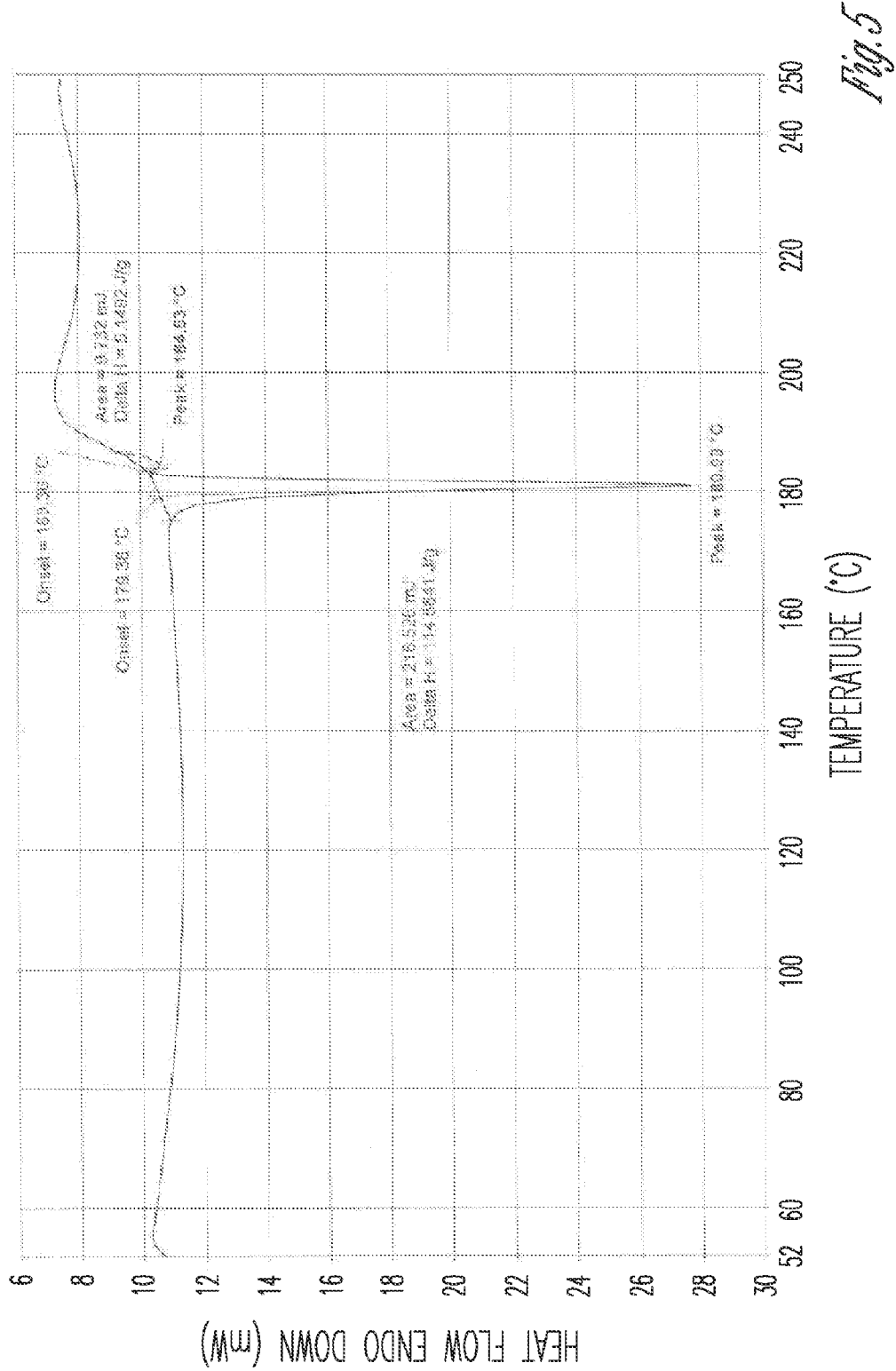
FIG. 5: DSC of R-(+)-Rasagiline hydrochloride Form I obtained according to present invention.

R-(+)-Rasagiline hydrochloride Form I obtained according to present invention is characterized by X-ray powder diffraction (XRPD), Infrared spectra (IR) and Differential Scanning calorimetry (DSC) [FIGS. 3, 4 and 5 respectively]. R-(+)-Rasagiline hydrochloride Form I obtained according to the present invention is further characterized by XRPD having peaks at 2-theta values of about 8.7985, 12.0679, 12.8598, 14.3054, 14.9722, 16.5380, 17.1203, 20.9926, 21.2559, 22.5973, 23.0420, 24.3110, 24.9157, 25.9406, 26.1127, 26.2943, 26.6900, 27.2790, 27.7949, 28.3579, 28.8551, 29.4137, 31.8922, 32.4174, 33.3018, 34.5314, 35.1540, 35.5857, 35.8437, 36.4440, 36.8671, 37.5693, 38.2844, 38.8002, 38.9147, 41.1183, 43.0069, 44.0083, 46.4849, 47.1675, 48.3017 and 48.7839. R-(+)-Rasagiline hydrochloride Form I is characterized by Infrared absorption spectrum having bands at approximately 3214, 1589, 1415, 1374, 1322, 1048, 757, 709 and 566 cm$^{-1}$. It exhibits two endotherms, first in the range of about 179-181° C. followed by second at about 183-184° C. as depicted in FIG. 5. R-(+)-Rasagiline hydrochloride Form I obtained according to the present invention has water content in the range of 0.2-1.5% as determined by Karl-Fischer method.

Figure 6:
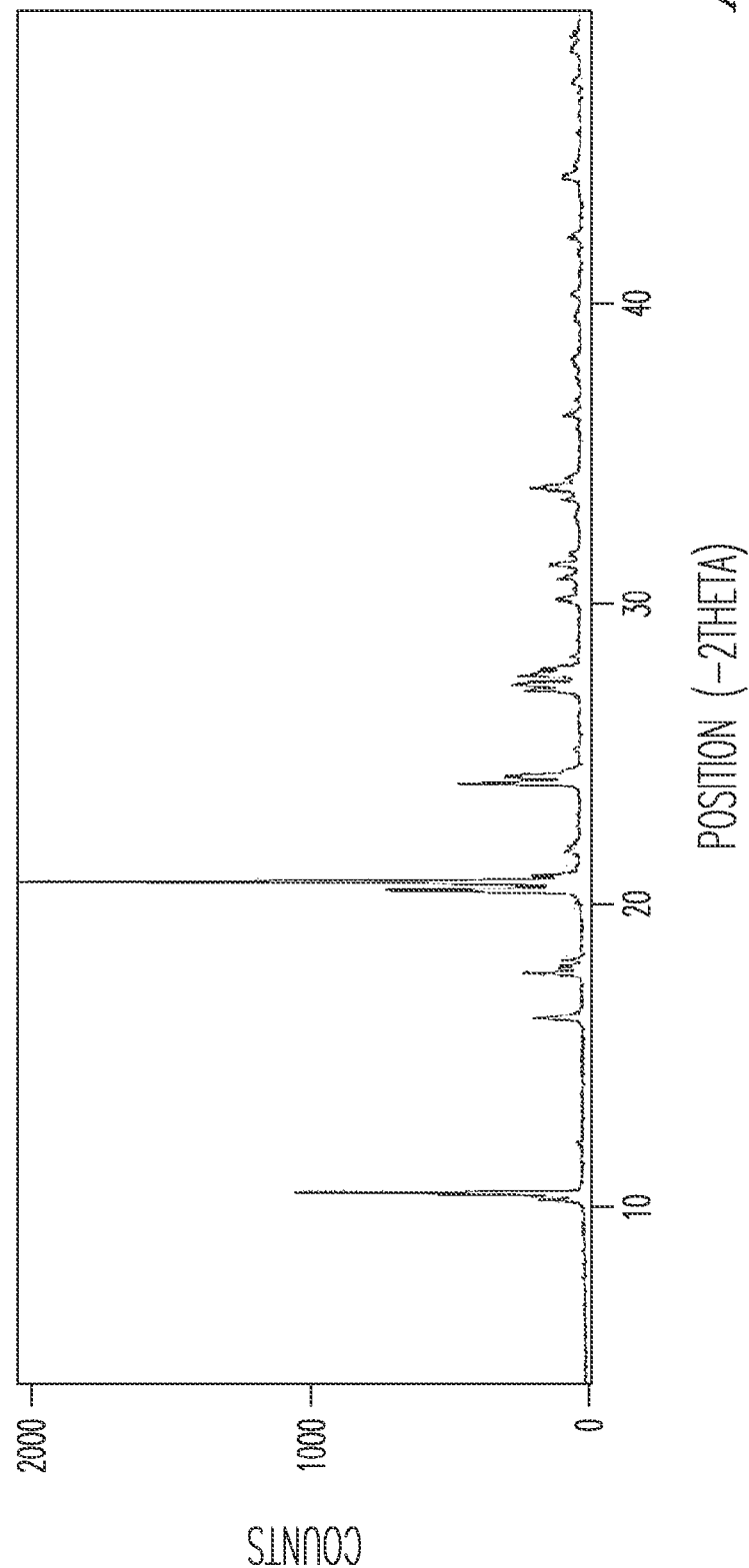
FIG. 6: X-ray powder diffraction pattern of R-(+)-Rasagiline hydrochloride Form II obtained according to present invention.
Figure 7:
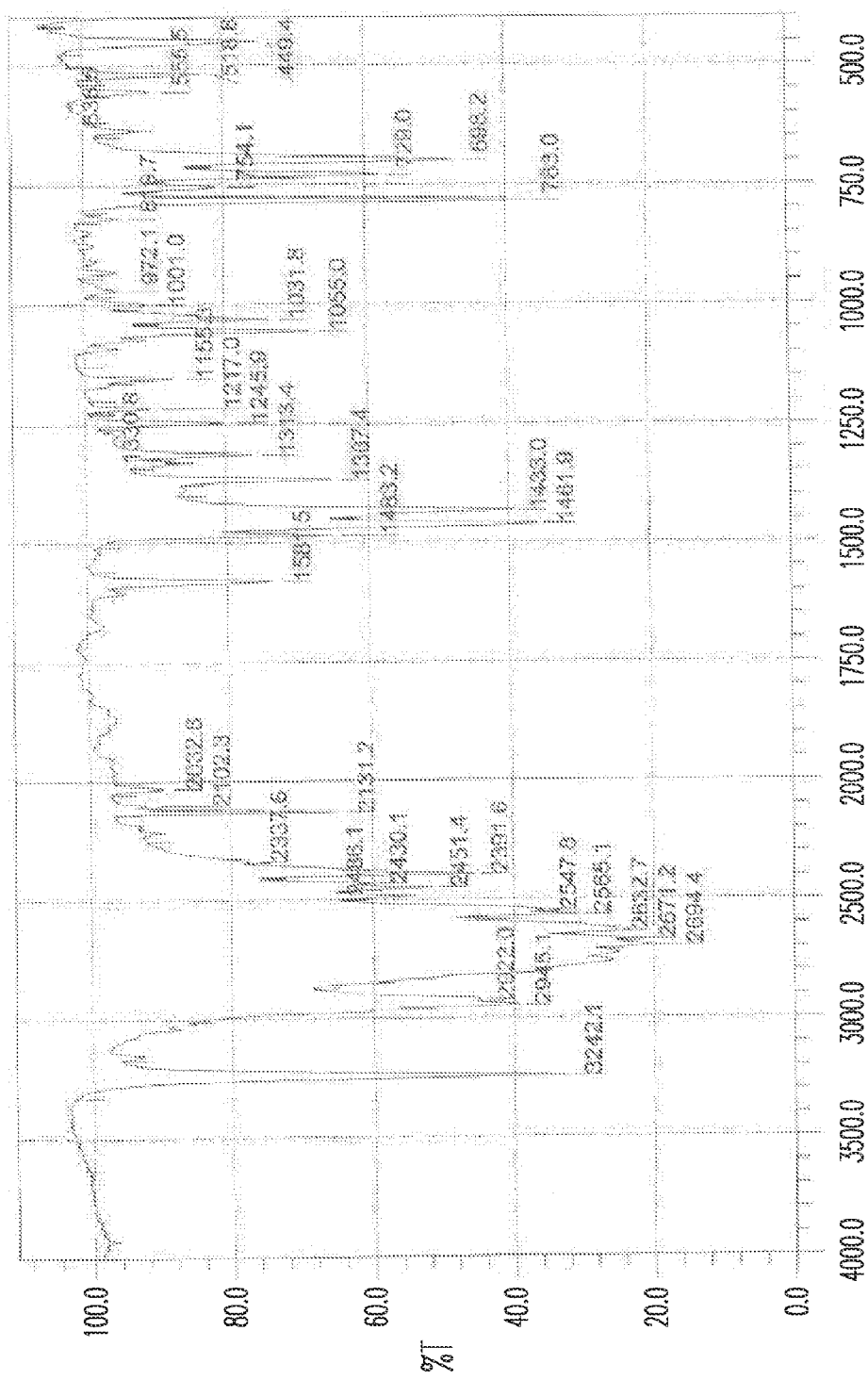
FIG. 7: FT-IR of R-(+)-Rasagiline hydrochloride Form II obtained according to present invention.
Figure 8:
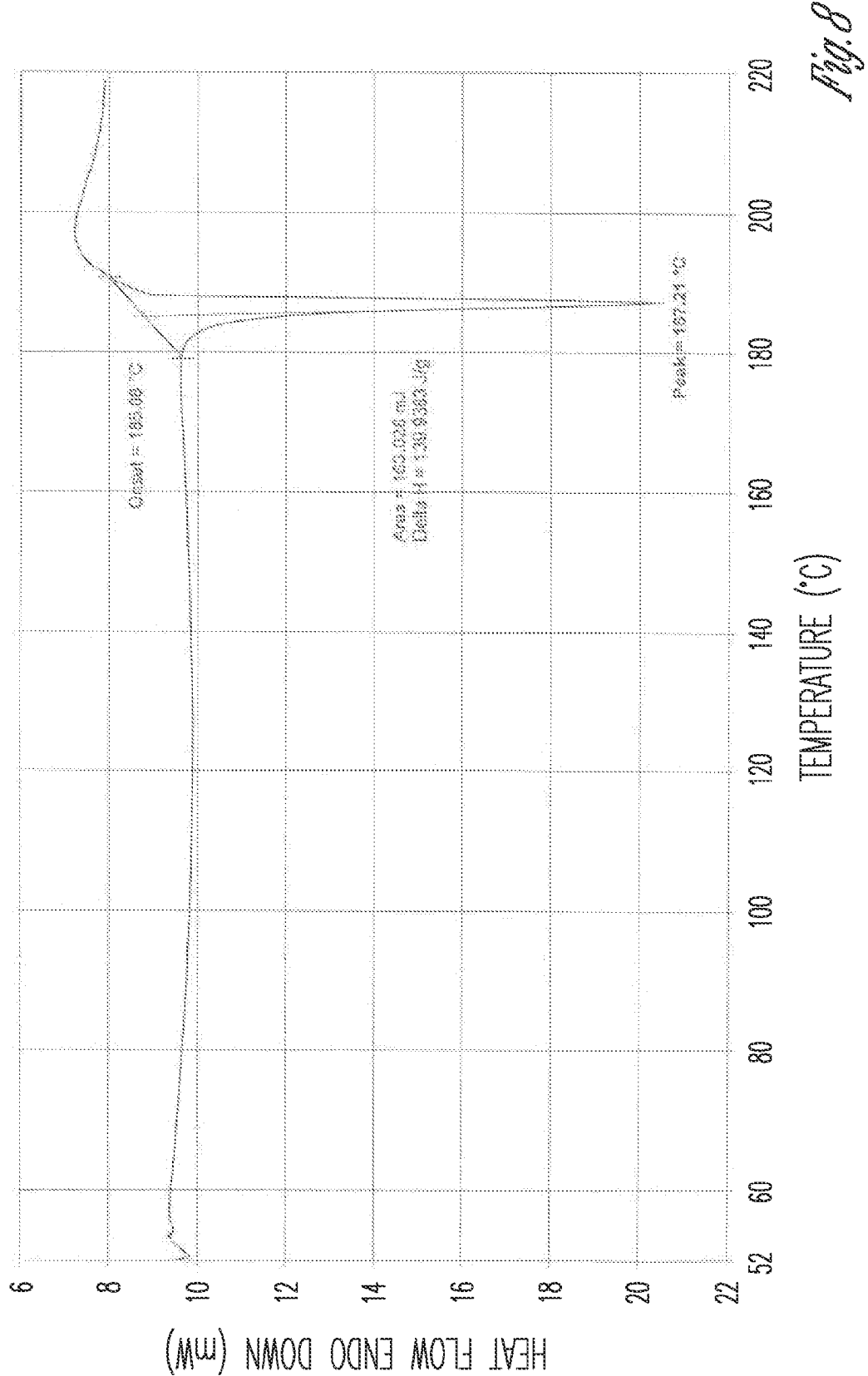
FIG. 8: DSC of R-(+)-Rasagiline hydrochloride Form II obtained according to present invention.

According to another embodiment the present invention provides polymorphic form of R-(+)-Rasagiline hydrochloride, Form II characterized by XRPD as depicted in FIG. 6. It is further characterized by XRPD having peaks at 2-theta values of about 10.1625, 10.4176, 16.1704, 17.7077, 18.1472, 20.4639, 20.7335, 20.9827, 21.8395, 24.0818, 24.3212, 27.1817, 27.3818, 27.6928, 30.2164, 30.9548, 31.3861, 33.5375, 33.9265, 36.3664, 38.1759, 39.6696, 40.4037, 42.3227, 44.3113, 47.5882 and 48.6140. R-(+)-Rasagiline hydrochloride Form II is characterized by IR spectrum as depicted in FIG. 7. It is further characterized by bands at approximately 3242, 1581, 1483, 1461, 1433, 1367, 1313, 1055, 783, 729, 698 and 555 cm$^{-1}$. It exhibits a single endotherm in the range of about 185-187° C. as depicted in FIG. 8. R-(+)-Rasagiline hydrochloride Form II obtained according to the present invention has water content in the range of 4.5-6.5% as determined by Karl-Fischer method.

Another embodiment of the present invention provides process for the preparation of novel crystalline Form II of R-(+)-Rasagiline hydrochloride comprising:
a) dissolving Rasagiline hydrochloride in a first solvent to obtain a solution;
b) optionally, adding a second solvent to the solution of step a); and
c) isolating R-(+)-Rasagiline hydrochloride Form II.

The dissolution is carried out at temperature of 50-100° C. or at the reflux temperature of the solvent selected for dissolution. The solution is optionally filtered to remove insoluble/suspended impurities. In solvent-antisolvent method, the solution is optionally cooled to a temperature of about −10 to 5° C. for 4-5 hrs before or after adding second solvent to get the desired product.

The first solvent used is selected from alcohol, nitrile, ketone, chlorinated hydrocarbon, water or mixture thereof. Alcohol is selected from $C_{1-4}$ alcohol such as methanol, ethanol or isopropyl alcohol. Nitrile is selected from $C_{1-4}$ nitriles such as acetonitrile or propionitrile. Chlorinated hydrocarbon is selected from methylene dichloride, ethylene dichloride, carbon tetrachloride or chloroform. Ketone is selected from acetone, 2-butanone or diethyl ketone. The second solvent is selected from aliphatic or aromatic hydrocarbon, ether, ester, ketone, water or mixture thereof. Aliphatic hydrocarbon is selected from pentane, hexane or heptane. Aromatic hydrocarbon is selected from toluene or xylene. Ether is selected from diethyl ether, methyl-t-butyl ether, diisopropyl ether, tetrahydrofuran or 1,4-dioxane. Ester is selected from $C_{1-6}$ ester such as methyl acetate, ethyl acetate or butyl acetate. Ketone is selected from acetone, 2-butanone or diethyl ketone.

According to another embodiment of the present invention, there is provided a process for drying R-(+)-Rasagiline hydrochloride Form I or Form II at temperature of about 50-70° C., preferably 60° C. for 6-26 hrs, preferably 12 hrs.

Rasagiline used for preparation of Form I and Form II of R-(+)-Rasagiline hydrochloride may be racemic Rasagiline base, Rasagiline hydrochloride, enantiomer thereof, any salt thereof or any polymorph thereof.

Rasagiline hydrochloride obtained according to the present invention has high chiral purity, ee >99.9%; chemical purity >99.5% and polymorphic purity >99%. R-(+)-Rasagiline hydrochloride obtained according to present invention have 90% particles less than 500 microns preferably less than 300 microns which may be micronized using conventional micronization techniques to get reduced particle size. Preferably, particle size distribution of R-(+)-Rasagiline hydrochloride is as follows, $d_{90}$ is between 40-80μ, $d_{50}$ is between 10-20μ and $d_{10}$ is between 2-9μ. Specific surface area of R-(+)-Rasagiline hydrochloride is atleast about 1 m²/g or more. Micronized R-(+)-Rasagiline hydrochloride has particle size distribution such that 90% of the total amount by volume of R-(+)-Rasagiline hydrochloride particles have size less than 20 microns, preferably less than 10 microns. Preferably micronized R-(+)-Rasagiline hydrochloride has particle size distribution such that 90% of the particles have particle size less than or equal to 9μ and/or 50% of the particles have particle size less than or equal to 4μ.

Figure 9:
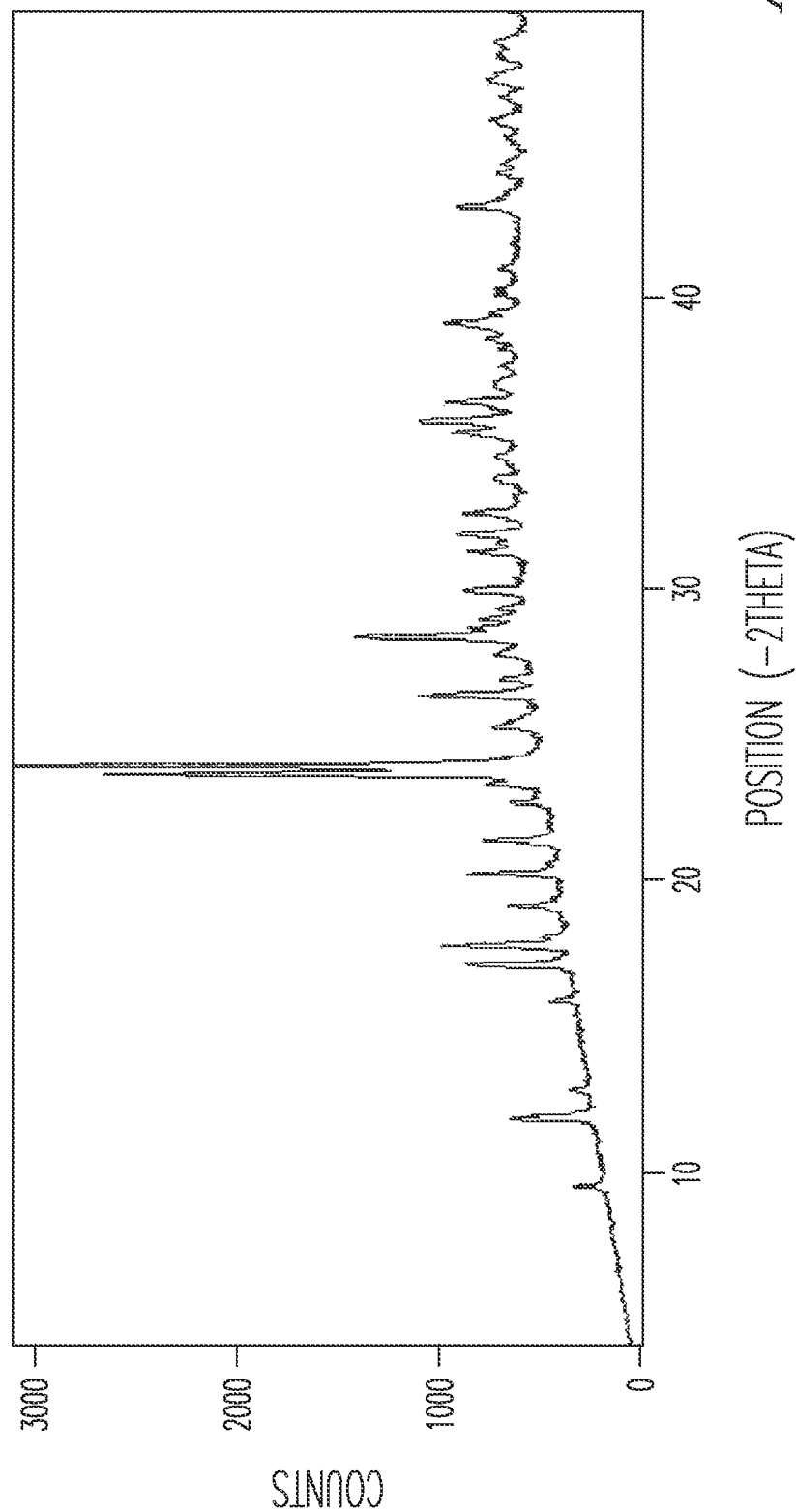
FIG. 9: X-ray powder diffraction pattern of R(+)-Rasagiline hydrobromide obtained according to the present invention.

According to another embodiment, the present invention provides R(+)-Rasagiline hydrobromide characterized by an X-ray powder diffraction pattern as shown in FIG. 9. R(+)-Rasagiline hydrobromide obtained according to the present invention is further characterized by X-ray diffraction peaks at 2θ values of about: 11.78, 17.03, 17.67, 20.16, 23.62, 23.91, 26.33, 28.33 and 35.70.

Another embodiment of the present invention provides process for preparation of R(+)-Rasagiline hydrobromide which comprises,
a) reacting R(−)-1-aminoindan or salt thereof with propargyl benzenesulfonate in aqueous medium in presence of a base and optionally in presence of phase transfer catalyst to get R(+)-Rasagiline; and
b) converting the obtained R(+)-Rasagiline to R(+)-Rasagiline hydrobromide.

The particle size distribution of R(+)-Rasagiline hydrobromide, measured by dry method is as follows; $d_{90}$ is 40-80μ, $d_{50}$ is between 10-20μ and $d_{10}$ is about 2-9μ. R(+)-Rasagiline hydrobromide thus obtained is micronized by conventional micronization techniques to have particle size distribution (measured by dry method) such that 90% of the total amount by volume of R-(+)-Rasagiline hydrobromide particles have size less than 20 microns, preferably less than 10 microns. Preferably, $d_{90}$ is about 4-9μ, $d_{50}$ is about 2-4μ and $d_{10}$ is about 1-2μ.

R(+)-Rasagiline hydrobromide obtained according to the present invention is substantially free from N-2-Propene-1-yl-2-bromo-(R)-aminoindan hydrobromide (Impurity A) and/or N-2-Propene-1-yl-3-bromo-(R)-aminoindan hydrobromide (Impurity B).

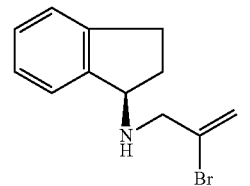

Impurity A

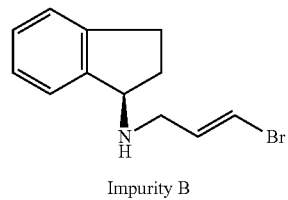

Impurity B

According to another embodiment of the present invention, there is provided impurity A. i.e., N-2-Propene-1-yl-2-bromo-(R)-aminoindan hydrobromide and impurity B N-2-Propene-1-yl-3-bromo-(R)-aminoindan hydrobromide.

Another embodiment of the present invention provides synthesis of Impurity A and/or Impurity B and use thereof as reference marker/reference standard. Another aspect of the present invention provides analytical method for testing the impurity profile of Rasagiline or pharmaceutically acceptable salt thereof, in particular Rasagiline hydrobromide, using Impurity A and/or Impurity B as reference marker/reference standard.

Figure 10:
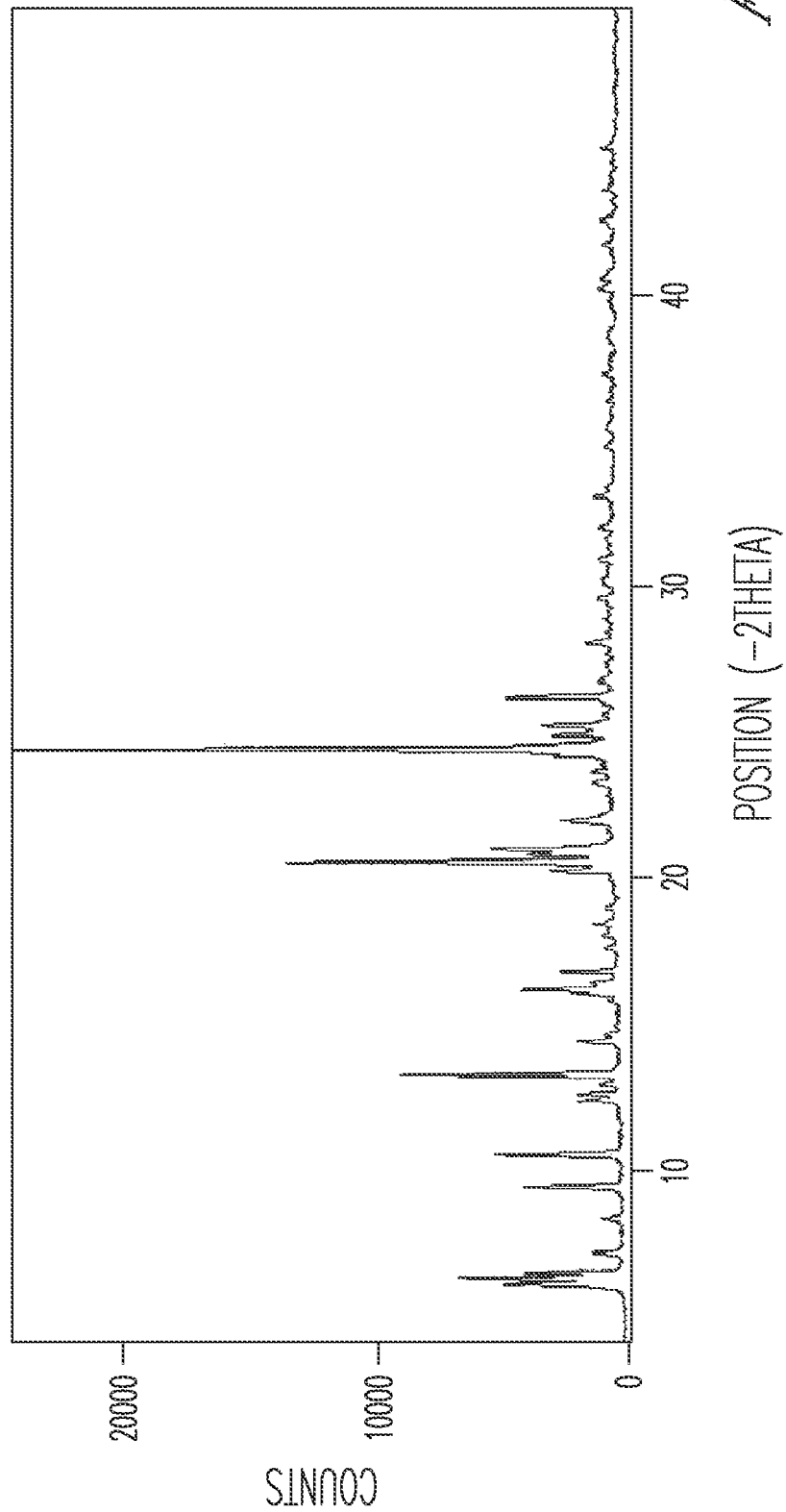
FIG. 10: X-ray powder diffraction pattern of R(+)-Rasagiline palmitate obtained according to the present invention.
Figure 11:
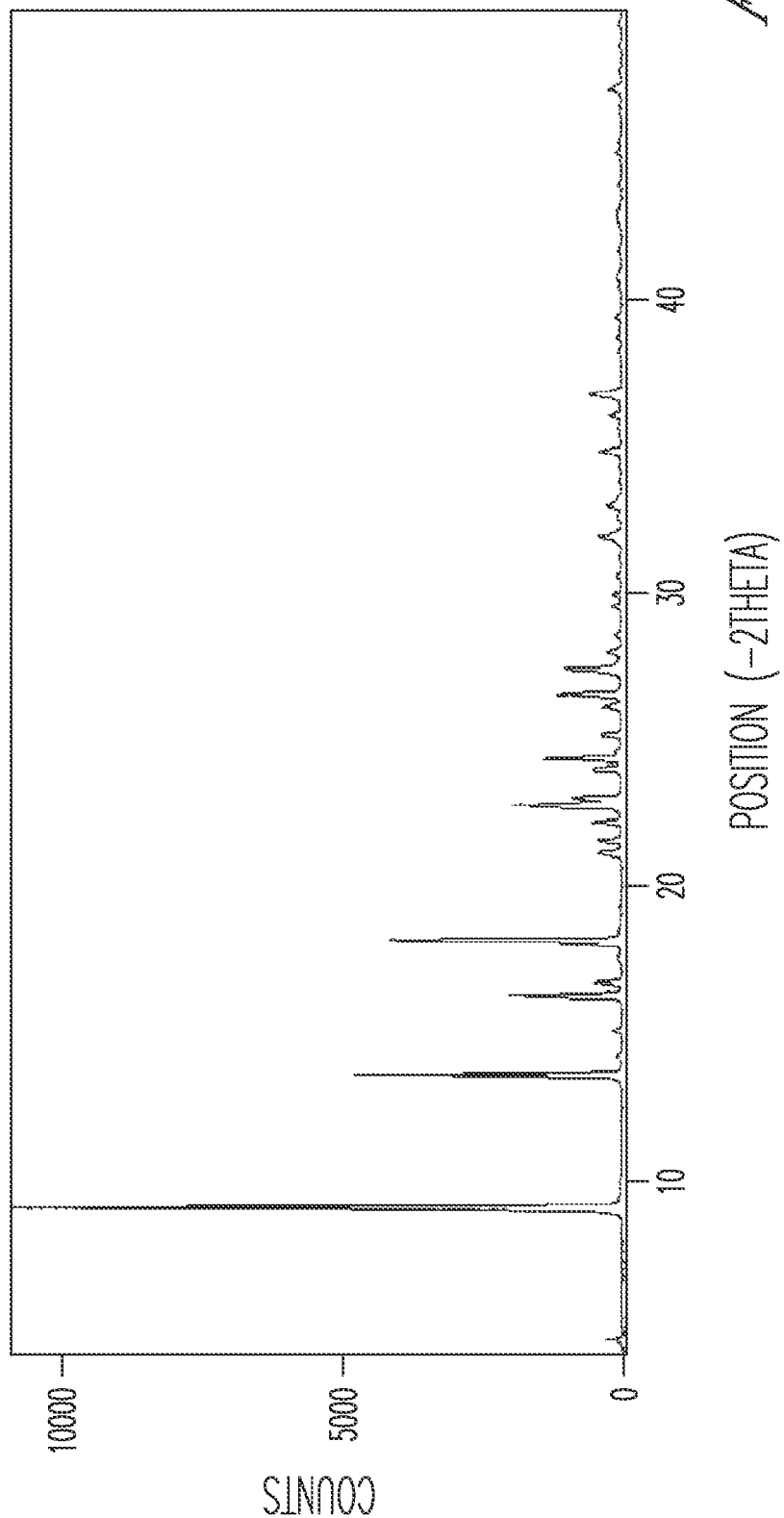
FIG. 11: X-ray powder diffraction pattern of R(+)-Rasagiline mesylate obtained according to U.S. Pat. No. 5,532,415.

According to another embodiment, the present invention provides palmitate salt of R(+)-Rasagiline characterized by X-ray diffraction pattern as shown in FIG. 10. R(+)-Rasagiline palmitate obtained according to the present invention is further characterized by X-ray diffraction peaks at 2θ values of about: 6.05, 6.27, 6.41, 9.34, 10.50, 13.22, 16.14, 20.22, 20.52, 21.02, 24.46 and 26.22.

Another embodiment of the present invention provides process for preparation of R(+)-Rasagiline palmitate which comprises,
a) reacting R(−)-1-aminoindan or salt thereof with propargyl benzenesulfonate in aqueous medium in presence of a base and optionally in presence of phase transfer catalyst to get R(+)-Rasagiline base; and
b) converting the obtained R(+)-Rasagiline base to R(+)-Rasagiline palmitate.

According to another embodiment of the present invention, there is provided a pharmaceutical composition of Rasagiline or pharmaceutically acceptable salt thereof, in particular Rasagiline mesylate or Rasagiline hydrobromide. Rasagiline mesylate or Rasagiline hydrobromide is blended with pharmaceutically acceptable excipient to obtain a blend. The obtained blend is then lubricated and the lubricated blend is then formulated into a finished dosage form. This finished dosage form may be in the form of tablet, capsule, granules, powder or syrup, preferably tablet. Preferably, $d_{90}$ of Rasagiline mesylate or Rasagiline hydrobromide used for the formulation is 10 microns.

Advantages of the present invention are:
a) N-alkylation reaction is carried out in aqueous media thereby avoiding use of organic solvents and tedious workup of the reaction mixture.
b) Use of phase transfer catalyst reduces the reaction time.
c) Provides consistent method for particle size determination of Rasagiline salts.
d) Overall yield according to the present invention is about 62%.

Further studies related to Rasagiline salts or polymorphs thereof are under progress.

Unless otherwise indicated, the following definitions are set forth to illustrate and define the meaning and scope of the various terms used to describe the invention herein.

The term "substantially free" means a compound having less than about 1%, preferably less than about 0.5%, more preferably less than about 0.3%, most preferably less than about 0.15% of undesired impurities or other polymorphic forms.

The term "reflux temperature" means the temperature at which the solvent or solvent system refluxes or boil at atmospheric pressure.

The term "micronization" means a process or method by which the size of particles are reduced.

The term "micron" refers to 'micrometer' which is $1 \times 10^{-6}$ meter.

The term "micronized" refers to particles having reduced particle size irrespective of the method employed for particle size reduction.

The term "pharmaceutically acceptable" means that which is useful in preparing a pharmaceutical composition that is generally non-toxic and is not biologically undesirable and includes that which is acceptable for human pharmaceutical use. As used herein, the term "room temperature" means a temperature from about 10° C. to 45° C., preferably 25° C. to 30° C.

General Experimental Conditions
X-Ray Powder Diffraction (XRPD)

X-ray powder diffraction pattern were obtained on Xpert'PRO, PANalytical, diffractometer equipped with accelerator detector using Copper Kα (n=1.5406 A°) radiation with scanning range between 4-50 2θ at a scanning speed of 2°/min.

Differential Scanning Calorimeter (DSC)

Differential Scanning calorimetry was performed on Diamond DSC of Perkin Elmer instrument. Samples of 2 mg to 3 mg weighed in aluminum crucibles with holes were scanned at a heating rate of 10° C. per minute under nitrogen atmosphere at rate of 35 ml/min.

Fourier Transform Infrared (FTIR)

The FT-IR spectra were obtained on Shimadzu FTIR 8300 in the range of 400-4000 $cm^{-1}$ with a resolution of 4 $cm^{-1}$.

The following examples are for illustrative purposes only and are not intended, nor should they be interpreted, to limit the scope of the invention in any manner.

EXAMPLES

Example 1

Preparation of (1R)-2,3-dihydro-N-2-propynyl-1H-indane-1-amine (Rasagiline Base Crude)

900 ml water was charged in a round bottom flask at room temperature followed by addition of NaOH pellets (70.5 g) and tetrabutyl ammonium bromide (6 g) under stirring. After completion of addition, the reaction mixture was cooled to 15-20° C. R-(−)-1-aminoindan hydrochloride (150 g) was charged and the mixture was stirred for 15 min followed by dropwise addition of propargyl benzenesulfonate (180 g) to the reaction mixture over a period of 45 min. The reaction mixture was stirred at 15-20° C. for 2 hr. The reaction mass was checked on TLC for completion of reaction. 1 L of toluene was charged to the reaction mass and stirred for 30 min. The toluene layer was separated and washed with 10% aqueous NaOH solution. The aqueous layer was again extracted with 500 ml of toluene. The combined toluene layer was washed with water (2×500 ml). 250 ml of water was added to the toluene layer and the mixture was cooled to 15-20° C. followed by dropwise addition of 10% aqueous sulfuric acid solution to attain pH 3. The toluene layer was separated and washed with 500 ml water. The combined aqueous layer was washed with toluene (2×250 ml). The aqueous layer was cooled to 15-20° C. and 10% aqueous NaOH solution was added dropwise till pH 8. The reaction mixture was charged with 500 ml of toluene and stirred for 30 min. The toluene layer was separated and aqueous layer was extracted with 250 ml of toluene. The combined toluene layer was washed with (2×500 ml) water. The separated toluene layer was dried over anhydrous sodium sulfate and distilled off under vacuum at 65° C. to get (90 g, 60%) of the title compound as an oil.

Example 2

Purification of (1R)-2,3-dihydro-N-2-propynyl-1H-indane-1-amine (Rasagiline Base Pure)

Rasagiline base crude (dissolved in methylene dichloride) was purified by column chromatography using neutral alumina as a stationary phase and hexane-ethyl acetate (90:10) mixture as mobile phase to get (81.0 g, 90%) of the title compound as an oil.

Example 3

Recovery of R(−)-aminoindan

The aqueous mother liquor obtained after separation of toluene layer (containing rasagiline base, Example 1) was basified to pH 12 using 10% aq. NaOH (100 ml). 500 ml of toluene was charged to the above mixture and the reaction mass was stirred for 30 min. The toluene layer was separated and the aqueous layer was extracted with 250 ml of toluene. The combined toluene layers were washed with (2×500 ml) water. The toluene layer was separated, dried over anhydrous sodium sulfate and distilled under vacuum at 65° C. to get (15 g, 10%) of the title compound as an oil.

Example 4

Preparation of (1R)-2,3-dihydro-N-2-propynyl-1H-indane-1-amine mesylate (Rasagiline Mesylate)

Rasagiline base (81 g, 0.47 moles) was dissolved in IPA (810 ml) under stirring and the obtained solution was cooled to 5° C. A solution of methanesulfonic acid (0.49 moles, 47.7 g) in IPA (95 ml) was added dropwise to the above cooled solution. After complete addition, the mixture was stirred for 30 min at 5-10° C. to get the solid which was filtered and dried to get (105 g, 83%) of Rasagiline mesylate.

Example 5

Preparation of (1R)-2,3-dihydro-N-2-propynyl-1H-indane-1-amine mesylate (Rasagiline Mesylate)

Rasagiline tartrate (15.0 g, 0.046 moles) was added to IPA (150 ml) under stirring followed by addition of methanesulfonic acid (6.0 g, 0.06 moles). The mixture was heated to reflux for 45 min. and cooled to room temperature. The mixture was further cooled to 5-10° C. and stirred for 45 min. The obtained solid was filtered and dried to get (18 g, 83%) of the title compound.

Example 6

Preparation of (1R)-2,3-dihydro-N-2-propynyl-1H-indane-1-amine hydrochloride (Rasagiline Hydrochloride)

A] The oil obtained in example 2 (81 g, 0.47 moles) was dissolved in TA (810 ml) under stirring and the obtained solution was cooled to 5° C. A solution of HCl in IPA (200 ml) was added drop-wise to the above cooled solution. After complete addition, the mixture was stirred for 30 min at 5-10° C. and the obtained solid was filtered to get (86.5 g, 85%) Rasagiline hydrochloride.

B] The oil obtained in example 2 (10 g) was dissolved in methyl tertiary butyl ether (150 ml) and the solution was cooled to 10-15° C. under stirring. The reaction mixture was purged with hydrochloride gas till the pH of the reaction mixture was acidic and then stirred at 10-15° C. for 30 min. The product precipitated was collected by filtration, washed with methyl tertiary butyl ether to neutral pH to obtain 12 g (yield: 99%) of the title compound.

C] The oil obtained in example 2 (15 g) was dissolved in diethyl ether (300 ml) and the solution was cooled to 10-15° C. under stirring. The reaction mixture was purged with hydrochloride gas till the pH of the reaction mixture was acidic and then stirred at 10-15° C. for 30 min. The precipitated product was collected by filtration, washed with diethyl ether till neutral pH to obtain 17.7 g (yield: 97%) of the title compound.

Process for Preparation of R(+)-Rasagiline Hydrochloride Form I

Example 7

0.5 g of Rasagiline hydrochloride was taken in 10 ml of methanol and refluxed for 15-20 minutes to get clear solution. The hot solution was filtered and cooled to 25-30° C. The obtained solution was stirred at the same temperature for 4-5 hrs. The separated solid was filtered and dried at 60° C. to get R-(+)-Rasagiline hydrochloride Form I.

Example 8

0.5 g of Rasagiline hydrochloride was dissolved in 20 ml ethanol at reflux temperature and the solution was refluxed for 15-20 minutes to get clear solution. The hot clear solution was filtered and cooled to 25-30° C. The solution was stirred at the same temperature for 4-5 hrs. The separated solid was filtered and dried at 60° C. to get R-(+)-Rasagiline hydrochloride Form I.

Example 9

0.5 g of Rasagiline hydrochloride was dissolved in 20 ml isopropyl alcohol (IPA) at reflux temperature and the solution was refluxed for 15-20 minutes to get clear solution. The hot clear solution was filtered and cooled to 25-30° C. The solution was stirred at the same temperature for 4-5 hrs. The separated solid was filtered and dried at 60° C. to get R-(+)-Rasagiline hydrochloride Form I.

Example 10

0.5 g of Rasagiline hydrochloride was dissolved in 20 ml acetonitrile at reflux temperature and the solution was refluxed for 15-20 minutes to get clear solution. The hot clear solution was filtered and cooled to 25-30° C. The solution was stirred at the same temperature for 4-5 hrs. The separated solid was filtered and dried at 60° C. to get R-(+)-Rasagiline hydrochloride Form I.

Example 11

0.5 g of Rasagiline hydrochloride was taken in 10 ml methanol and refluxed for 15-20 minutes. The hot solution was filtered and cooled to 25-30° C. followed by addition of 20 ml acetone with stirring at the same temperature for 4-5 hrs. The separated solid was filtered and dried at 60° C. to get R-(+)-Rasagiline hydrochloride Form I.

Example 12

0.5 g of Rasagiline hydrochloride was taken in 10 ml methylene dichloride (MDC) and refluxed for 15-20 minutes. The hot solution was filtered and cooled to 25-30° C. followed by addition of 20 ml hexane with stirring at the same temperature for 4-5 hrs. The separated solid was filtered and dried at 60° C. to get R-(+)-Rasagiline hydrochloride Form I.

Example 13

0.5 g of Rasagiline hydrochloride was taken in 10 ml MDC and refluxed for 15-20 minutes. The hot solution was filtered and cooled to 25-30° C. followed by addition of 20 ml THF with stirring at the same temperature for 4-5 hrs. The separated solid was filtered and dried at 60° C. to get R-(+)-Rasagiline hydrochloride Form I.

Example 14

0.5 g of Rasagiline hydrochloride was taken in 10 ml MDC and refluxed for 15-20 minutes. The hot solution was filtered and cooled to 25-30° C. followed by addition of 20 ml ethyl acetate with stirring at the same temperature for 4-5 hrs. The separated solid was filtered and dried at 60° C. to get R-(+)-Rasagiline hydrochloride Form I.

Example 15

0.5 g of Rasagiline hydrochloride was taken in 10 ml methanol and refluxed for 15-20 minutes. The hot solution was filtered and cooled to 25-30° C. followed by addition of 20 ml DIPE with stirring at the same temperature for 4-5 hrs. The separated solid was filtered and dried at 60° C. to get R-(+)-Rasagiline hydrochloride Form I.

Process for Preparation of R(+)-Rasagiline Hydrochloride Form II

Example 16

0.5 g of Rasagiline hydrochloride was dissolved in 10 ml methanol at reflux temperature. The obtained solution was refluxed for 15-20 minutes to get clear solution. The hot clear solution was filtered and cooled rapidly to 0 to 5° C. followed by addition of 20 ml of MTBE to the obtained clear solution and the solution was stirred at −5 to 0° C. for 4-5 hrs. The separated solid was filtered and dried at 60° C. to get R-(+)-Rasagiline hydrochloride Form II.

Example 17

1 gram of Rasagiline hydrochloride was dissolved in 10 ml acetonitrile at reflux temperature. The obtained solution was refluxed for 15-20 minutes to get clear solution. The hot clear solution was filtered and cooled rapidly to −5 to 0° C. 50 ml of MTBE was added to the cooled clear solution and the solution was stirred at −5 to 0° C. for 4-5 hrs. The separated solid was filtered and dried at 60° C. to get R-(+)-Rasagiline hydrochloride Form II.

Example 18

1 gram of Rasagiline hydrochloride was dissolved in 10 ml methanol at reflux temperature. The solution was refluxed for 15-20 minutes to get clear solution. The hot clear solution was filtered to previously cooled 50 ml n-hexane at −5 to 0° C. and the was stirred at −5 to 0° C. for 4-5 hrs. The separated solid was filtered and dried at 60° C. to get R-(+)-Rasagiline hydrochloride Form II.

Example 19

1 gram of Rasagiline hydrochloride was dissolved in 10 ml methanol at reflux temperature. The solution was refluxed for 15-20 minutes to get clear solution. The hot clear solution was filtered to previously cooled 20 ml of ethyl acetate at −15° C. and the solution was stirred at −5 to 0° C. for 4-5 hrs. The separated solid was filtered and dried at 60° C. to get R-(+)-Rasagiline hydrochloride Form II.

Example 20

1 gram of Rasagiline hydrochloride was dissolved in 20 ml 1,4-dioxane and 5 ml MDC at reflux temperature. The solution was refluxed for 15-20 minutes to get clear solution. The hot solution was filtered, cooled and the solution was stirred at −5 to 0° C. for 4-5 hours. The obtained solution was filtered and dried at 60° C. to get R-(+)-Rasagiline hydrochloride Form II.

Example 21

1 gram of Rasagiline hydrochloride was dissolved in 10 ml acetone and 2 ml of water at reflux temperature. The obtained solution was concentrated under vacuum. The obtained solid was filtered to get R-(+)-Rasagiline hydrochloride Form II.

Example 22

Preparation of (1R)-2,3-dihydro-N-2-propynyl-1H-indane-1-amine hydrobromide (Rasagiline Hydrobromide)

Rasagiline base (81 g, 0.47 moles) was dissolved in IPA (810 ml) under stirring to obtain a solution. The obtained solution was cooled to 5° C. A solution of HBr in IPA (200 ml) was added dropwise to the cooled solution and stirred for 30 min at 5-10° C. The obtained solid was filtered and dried to get (112 g, 90%) of the title compound.

Example 23

Preparation of N-2-Propene-1-yl-2-bromo-(R)-aminoindan hydrobromide (Impurity A) and N-2-Propene-1-yl-3-bromo-(R)-aminoindan hydrobromide (Impurity B)

(R)-Rasagiline base pure (30 g) was dissolved in HBr (250 ml) and the solution was heated to reflux for 36 h. After the completion of reaction the mixture was cooled, diluted with water (500 ml) and slowly the solution was basified using aqueous ammonia solution. The mixture was extracted with methyl tertiary butyl ether (MTBE). The separated MTBE layer was evaporated to get a dark brown oil which exhibited 3 spots on TLC, two of which were of the desired compounds i.e., N-2-Propene-1-yl-2-bromo-(R)-aminoindan hydrobromide (Impurity A) and N-2-Propene-1-yl-3-bromo-(R)-aminoindan hydrobromide (Impurity B). The third spot had same Rf as that of the starting material i.e., the unreacted Rasagiline base. The products formed were separated by column chromatography (silica gel) using hexane-ethyl acetate mixture (75:25) as mobile phase to give pure N-2-Propene-1-yl-2-bromo-(R)-aminoindan (15% overall yield) and N-2-Propene-1-yl-3-bromo-(R)-aminoindan (15% overall yield).

The obtained N-2-Propene-1-yl-2-bromo-(R)-aminoindan (5 g) in 100 ml of MTBE was added to 10 ml of 10% HBr/IPA solution and the reaction mixture was stirred at 5-10° C. for 30 min. The precipitated solid was filtered, washed with MTBE and dried to give 8.7 g of N-2-Propene-1-yl-2-bromo-(R)-aminoindan hydrobromide (90% yield). Mass spectrum: [M+1]$^+$: 252

N-2-Propene-1-yl-3-bromo-(R)-aminoindan hydrobromide was synthesized by a similar process provided for synthesizing N-2-Propene-1-yl-2-bromo-(R)-aminoindan hydrobromide. Mass spectrum: [M+1]$^+$: 252

Example 24

Preparation of (1R)-2,3-dihydro-N-2-propynyl-1H-indane-1-amine palmitate (Rasagiline Palmitate)

Rasagiline base (81 g, 0.47 moles) was dissolved in IPA (810 ml) under stirring to obtain a solution. The obtained solution was cooled to 5° C. A solution of palmitic acid (0.49 moles, 125.6 g) in IPA (200 ml) was added dropwise to the cooled solution. After complete addition, the solution was stirred for 30 min at 5-10° C. The obtained solid was filtered and dried to get (172 g, 85%) of the title compound.

Example 25

Tablet Formulation of Rasagiline Hydrobromide

Mannitol (80.36 g), corn starch (24 g) and pregelatinised starch (12 g) were sifted through 60# sieve and mixed with Rasagiline Hydrobromide (0.74 g) in geometric proportion in a cone blender. The mixture was further sifted through 60# sieve to get a blend. This blend was mixed with pre-sifted (sifted through 40# sieve) colloidal silicon dioxide (1.2 g) and purified talc (1.2 g) for 5 minutes. Pre-sifted Stearic acid (0.5 g) (sifted through 40# sieve) was further added to the blend and lubricated for 2 minutes. The lubricated blend was compressed using suitable punches to get compressed tablets.

What is claimed is:

1. A process for preparation of R(+)-Rasagiline or pharmaceutically acceptable salt thereof comprising,
   a) reacting R(−)-1-aminoindan or a salt thereof with propargyl benzenesulfonate in aqueous medium at a temperature of 10-30° C. for about 2 to 4 hours in the presence of a base and a phase transfer catalyst to obtain a reaction mixture comprising R(+)-Rasagiline;
   b) optionally isolating R(+)-Rasagiline and/or unreacted R(−)-1-aminoindan from the reaction mixture;
   c) optionally converting R(+)-Rasagiline to pharmaceutically acceptable salt thereof.

2. The process of claim 1 wherein said reaction in step a) is carried out at a temperature of 15-20° C. for about 2 to 4 hours.

3. The process of claim 2 wherein said reaction is carried out in the presence of a base chosen from at least one of sodium hydroxide, potassium hydroxide, lithium hydroxide, sodium carbonate, potassium carbonate, sodium bicarbonate or potassium bicarbonate and a phase transfer catalyst chosen from at least one of tetrabutyl ammonium bromide, tetrabutyl ammonium chloride, tetrabutyl ammonium hydrogen sulphate, Aliquat 336, PEG-400 or PEG-600.

4. The process of claim 1 wherein said R(+)-Rasagiline is isolated and purified prior to converting to its pharmaceutically acceptable salt.

5. The process of claim 1 wherein said unreacted R(−)-1-aminoindan is isolated/recovered from the aqueous mother liquor obtained after isolation of R(+)-Rasagiline by treating said aqueous mother liquor with a base.

6. The process of claim 5 wherein said R(−)-1-aminoindan so isolated/recovered is converted to Rasagiline or pharmaceutically acceptable salt thereof.

7. The process of claim 6 wherein said pharmaceutically acceptable salt is selected from the group consisting of mesylate, hydrobromide, hydrochloride and palmitate.

8. The process of claim 7 wherein said pharmaceutically acceptable salt is in particulate form, and wherein the particle size is reduced to obtain particles having particle size distribution such that 90% of particles have particle size less than or equal to 9 um and/or 50% of particles have particle size less than or equal to 4 um.

9. The process of claim 8 wherein said pharmaceutically acceptable salt with reduced particle size is packed in a packaging material selected from glass bottle or polyethylene terephthalate (PET).

10. The process of claim 1, wherein R(+)-Rasagiline is isolated from the reaction mixture or converted to pharmaceutically acceptable salt thereof, and wherein the R(+)-Rasagiline or pharmaceutically acceptable salt thereof is substantially free of one or more of the impurities chosen from (1S)-2,3-dihydro-N-2-propynyl-1H-indane-1-amine, propargyl benzene sulfonate or isopropyl mesylate.

11. The process of claim 7 wherein R(+)-Rasagiline hydrobromide is prepared by treating R(+)-Rasagiline with HBr at a temperature of 5-10° C. and wherein the R(+)-Rasagiline hydrobromide is characterized by X-ray diffraction peaks at 2-theta values of about 11.78, 17.03, 17.67, 20.16, 23.62, 23.91, 26.33, 28.33 and 35.70 degrees.

12. The process of claim 11 wherein said R(+)-Rasagiline hydrobromide is substantially free of N-2-Propene-1-yl-2-bromo-(R)-aminoindan hydrobromide and/or N-2-Propene-1-yl-3-bromo-(R)-aminoindan hydrobromide.

13. The process of claim 12 wherein N-2-Propene-1-yl-2-bromo-(R)-aminoindan hydrobromide and/or N-2-Propene-1-yl-3-bromo-(R)-aminoindan hydrobromide is used as a reference marker and/or reference standard in determining purity of R(+)-Rasagiline or pharmaceutically acceptable salt thereof.

14. The process of claim 1, wherein said reaction mixture is subjected to solvent extraction to isolate R(+)-Rasagiline.

15. The process of claim 7 wherein R(+)-Rasagiline palmitate is prepared by treating R(+)-Rasagiline with palmitic acid at a temperature of 5-10° C. and wherein the R(+)-Rasagiline palmitate is characterized by X-ray diffraction peaks at 2-theta values of about: 6.05, 6.27, 6.41, 9.34, 10.50, 13.22, 16.14, 20.22, 20.52, 21.02, 24.46 and 26.22 degrees.

* * * * *

UNITED STATES PATENT AND TRADEMARK OFFICE
CERTIFICATE OF CORRECTION

| | | |
|---|---|---|
| PATENT NO. | : 8,741,962 B2 | Page 1 of 1 |
| APPLICATION NO. | : 12/954497 | |
| DATED | : June 3, 2014 | |
| INVENTOR(S) | : Sathe et al. | |

It is certified that error appears in the above-identified patent and that said Letters Patent is hereby corrected as shown below:

In the Claims

In column 21, line 21, in Claim 1, delete "comprising," and insert --comprising:--, therefor In column 22, line 4, in Claim 7, delete "6" and insert --1--, therefor In column 22, line 11, in Claim 8, delete "um" and insert --μm--, therefor In column 22, line 12, in Claim 8, delete "um" and insert --μm--, therefor In column 22, line 46, in Claim 15, delete "about:" and insert --about--, therefor Signed and Sealed this
Ninth Day of December, 2014

Michelle K. Lee
*Deputy Director of the United States Patent and Trademark Office*